United States Patent
Mann et al.

(10) Patent No.: US 9,744,353 B2
(45) Date of Patent: Aug. 29, 2017

(54) DETECTION OF PRESENCE AND ALIGNMENT OF A THERAPEUTIC AGENT IN AN IONTOPHORETIC DRUG DELIVERY DEVICE

(71) Applicant: NuPathe, Inc., Conshohocken, PA (US)

(72) Inventors: Ronalee Lo Mann, Menlo Park, CA (US); Jason Clevenger, Cambridge, MA (US); David Saar, Titusville, NJ (US)

(73) Assignee: Teva Pharmaceuticals International GmbH, Rapperswil-Jona (CH)

( * ) Notice: Subject to any disclaimer, the term of this patent is extended or adjusted under 35 U.S.C. 154(b) by 1233 days.

(21) Appl. No.: 13/677,089

(22) Filed: Nov. 14, 2012

(65) Prior Publication Data
US 2014/0135679 A1   May 15, 2014

(51) Int. Cl.
*A61N 1/30* (2006.01)
*A61N 1/32* (2006.01)
*A61N 1/04* (2006.01)

(52) U.S. Cl.
CPC .......... *A61N 1/303* (2013.01); *A61N 1/0428* (2013.01); *A61N 1/325* (2013.01); *Y10T 29/49117* (2015.01)

(58) Field of Classification Search
CPC ........ A61N 1/0428; A61N 1/303; A61N 1/30; A61N 1/325
See application file for complete search history.

(56) References Cited

U.S. PATENT DOCUMENTS

| | | | |
|---|---|---|---|
| 5,320,597 A * | 6/1994 | Sage, Jr. ................ | A61N 1/303 604/20 |
| 8,983,594 B2 | 3/2015 | Saar et al. | |
| 2002/0161324 A1 | 10/2002 | Henley et al. | |
| 2008/0058703 A1* | 3/2008 | Subramony .......... | A61K 9/0009 604/20 |
| 2008/0262414 A1* | 10/2008 | Barsness .............. | A61N 1/0428 604/20 |
| 2013/0296766 A1 | 11/2013 | Sebree et al. | |

FOREIGN PATENT DOCUMENTS

| | | |
|---|---|---|
| WO | 0062857 A1 | 10/2000 |
| WO | 2008027218 A2 | 3/2008 |

OTHER PUBLICATIONS

International Search Report and Written Opinion for International Application No. PCT/US2013/070068 mailed Jan. 28, 2014.

* cited by examiner

*Primary Examiner* — Imani Hayman
*Assistant Examiner* — Nilay Shah
(74) *Attorney, Agent, or Firm* — McCarter & English, LLP; Danielle L. Herritt, Esq.

(57) ABSTRACT

A system is provided for testing whether an iontophoretic drug delivery device is in an appropriate state for administering a therapeutic agent into an animal body. An electrical characteristic of at least one electrical path associated with an electrode test point is used to determine whether the iontophoretic device is in an appropriate state. The measured electrical characteristic indicates that the iontophoretic device is in an appropriate state for administering the therapeutic agent into the animal body when the therapeutic agent is properly disposed with respect to the electrodes of the iontophoretic device.

27 Claims, 23 Drawing Sheets

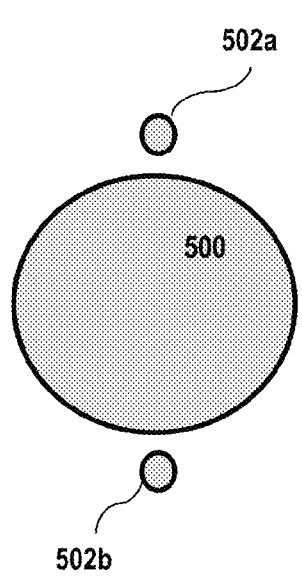
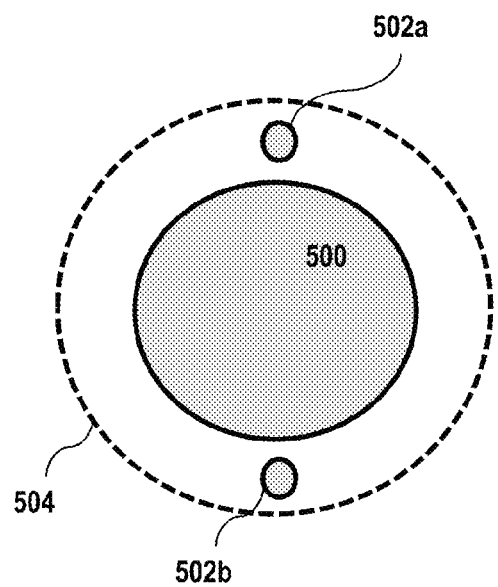
*Figure 5A*  *Figure 5B*
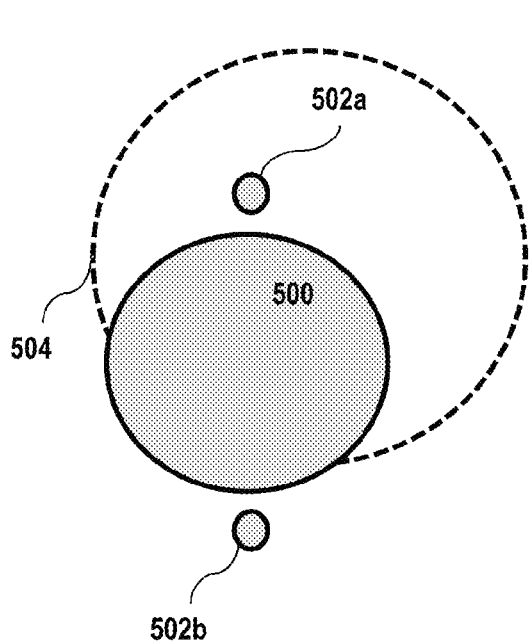
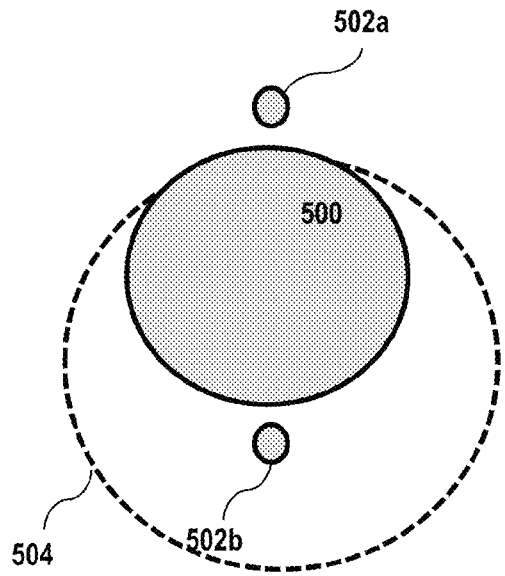
*Figure 5C*  *Figure 5D*

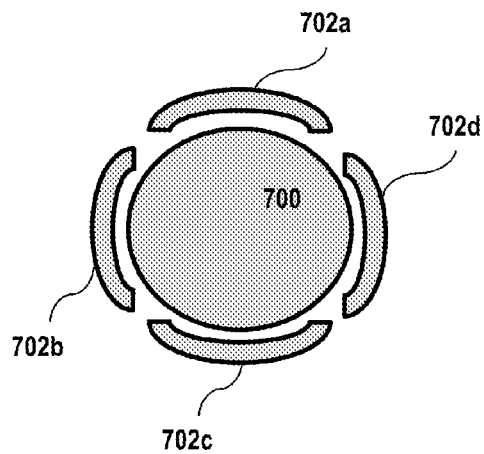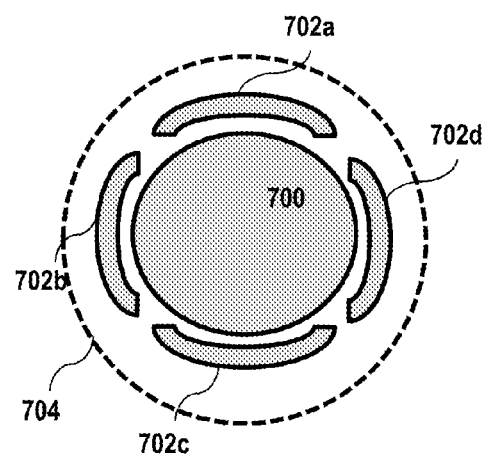
*Figure 7A*  *Figure 7B*
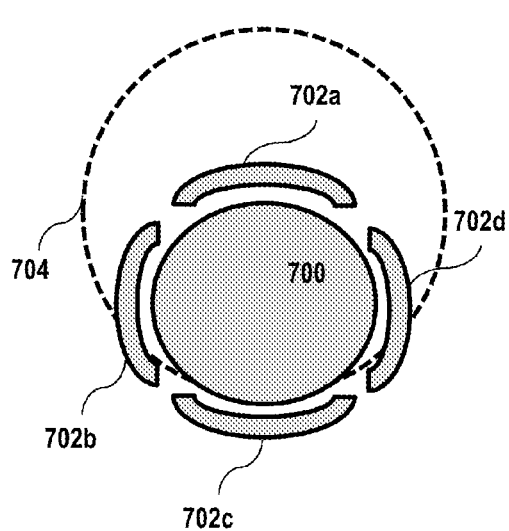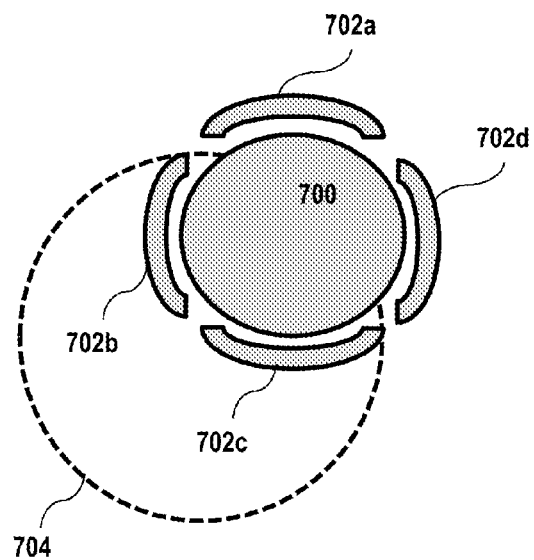
*Figure 7C*  *Figure 7D*

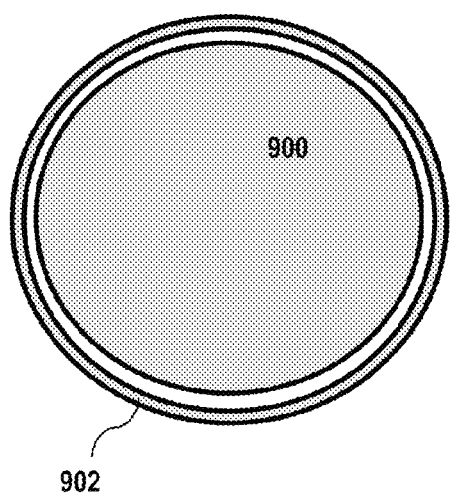
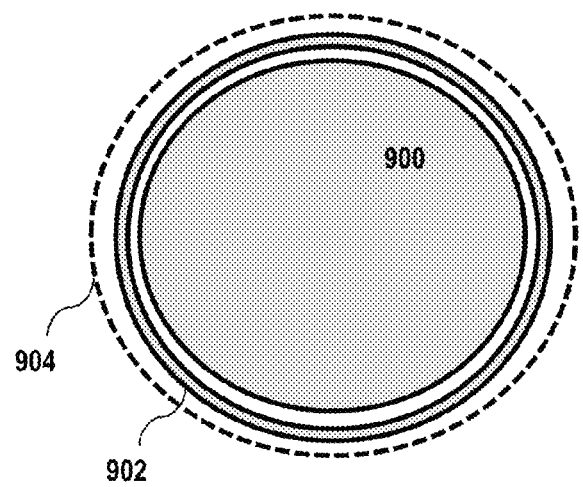
*Figure 9A*  *Figure 9B*
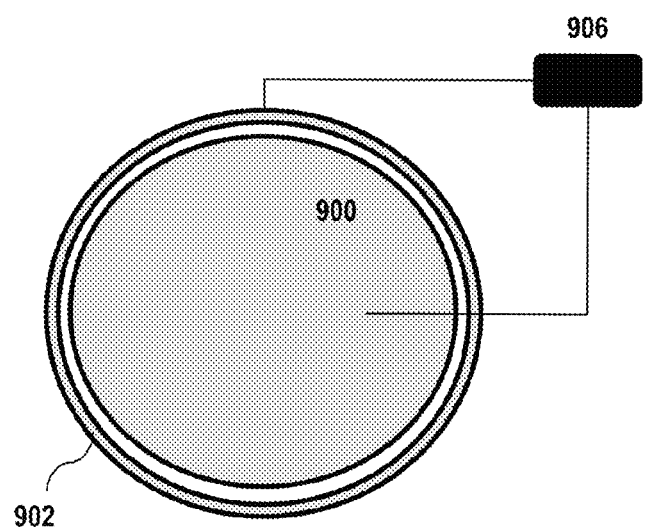
*Figure 9C*

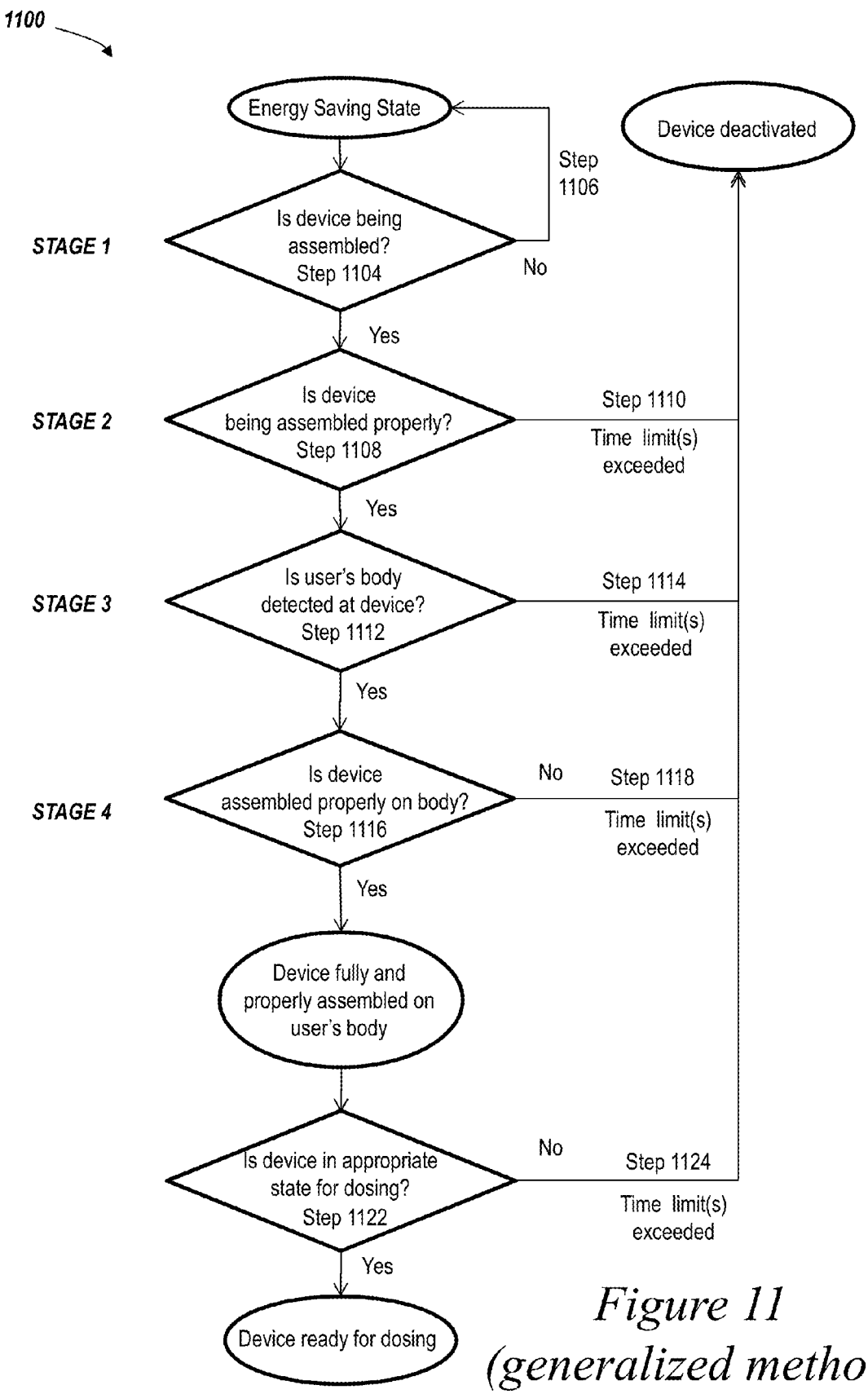
*Figure 11 (generalized method)*

DETECTION OF PRESENCE AND ALIGNMENT OF A THERAPEUTIC AGENT IN AN IONTOPHORETIC DRUG DELIVERY DEVICE

RELATED APPLICATIONS

This application is related to U.S. patent application Ser. No. 12/648,726, titled "Electronic Control of Drug Delivery System," filed Dec. 29, 2009, the entire contents of which are expressly incorporated herein by reference.

BACKGROUND

Drug delivery is a method or process of delivering a therapeutic agent or drug to achieve a therapeutic effect in an animal body. Certain drug delivery technologies employ iontophoresis to transdermally administer a therapeutic agent by using an electrotransport current to drive the therapeutic agent into the animal body. In a typical iontophoretic drug delivery device, a reservoir holding a therapeutic agent in a conductive medium is placed in contact with one of an anode or a cathode, and a reservoir holding a conductive salt solution is placed in contact with the other of the anode or the cathode. The reservoirs are typically placed in contact with the animal body and in contact with the corresponding electrodes, thus allowing a voltage difference established between the electrodes to drive an electrotransport current through the reservoirs into the animal body, thereby directly administering the therapeutic agent to the animal body.

SUMMARY

Exemplary embodiments provide at least one electrical test point associated with an electrode in an iontophoretic therapeutic agent delivery device. Some exemplary embodiments may provide one or more electrical test points associated with an anode and one or more electrical test points associated with a cathode in an iontophoretic therapeutic agent delivery device. Upon assembly of the device, proper positioning of a conductive reservoir over an associated electrode in the device may establish an electrical connection between the electrode and each of its one or more associated test points. In this exemplary configuration, when a conductive reservoir is missing from a corresponding electrode, electrical connections among the electrode and its one or more associated test points are non-existent or minimal. As such, detection of non-existent or minimal electrical connections between an electrode and its one or more associated test points indicates that a conductive reservoir is missing from the electrode. Conversely, detection of a non-negligible electrical connection between an electrode and each of its one or more associated test points may indicate that a conductive reservoir is present and properly positioned on the electrode. On the other hand, when a conductive reservoir is present but misaligned with an associated electrode, an electrical connection between the electrode and at least one of its one or more associated test points may be non-existent or minimal. As such, detection of a non-existent or minimal electrical connection between an electrode and at least one of its one or more associated test points may indicate that a conductive reservoir is misaligned with the electrode.

In accordance with one exemplary embodiment, a system is provided for testing whether an iontophoretic device is in an appropriate state for administering a therapeutic agent into an animal body by driving an electrotransport current through a surface of the animal body. The device includes at least one electrical test point and at least one electrical path leading from the at least one test point and configured to lead to an electrode of the iontophoretic device. The device also includes a controller programmed to measure an electrical characteristic of the at least one electrical path and determine whether the iontophoretic device is in an appropriate state for administering a therapeutic agent into an animal body from the measured electrical characteristic. The measured electrical characteristic indicates that the iontophoretic device is in the appropriate state for administering the therapeutic agent into the animal body when the therapeutic agent is properly disposed with respect to the iontophoretic device. The controller is also programmed to prevent use of the iontophoretic device if the iontophoretic device is not in an appropriate state for administering the therapeutic agent into the animal body within a predetermined period of time after a first measurement of the electrical characteristic. In an exemplary embodiment, the controller may prevent administration of the therapeutic agent by ensuring that a non-existent or minimal level of electrotransport current flows between the electrodes of the device.

In accordance with another exemplary embodiment, a system is provided for testing whether an iontophoretic device is in an appropriate state for administering a therapeutic agent into an animal body by driving an electrotransport current through a surface of the animal body. The device includes a first electrical test point and a second electrical test point and at least one electrical path leading from the first test point and configured to lead to the second test point. The device also includes a controller programmed to measure an electrical characteristic of the at least one electrical path and determine whether the iontophoretic device is in an appropriate state for administering a therapeutic agent into an animal body from the measured electrical characteristic. The measured electrical characteristic indicates that the iontophoretic device is in the appropriate state for administering the therapeutic agent into the animal body, when the therapeutic agent is properly disposed with respect to the iontophoretic device. The controller is also programmed to prevent use of the iontophoretic device if the iontophoretic device is not in an appropriate state for administering the therapeutic agent into the animal body within a predetermined period of time after a first measurement of the electrical characteristic. In an exemplary embodiment, the controller may prevent administration of the therapeutic agent by ensuring that a non-existent or minimal level of electrotransport current flows between the electrodes of the device.

In some embodiments, the controller is further programmed to determine whether the iontophoretic device is in an appropriate state for administering a therapeutic agent into an animal body from the measured electrical characteristic after the electrode is placed in direct or indirect contact with a surface of the animal body.

In some embodiments, the therapeutic agent is introduced into a reservoir before the reservoir is assembled with the electrode. In some embodiments, the therapeutic agent is introduced into a reservoir after the reservoir is assembled with the electrode.

In accordance with another exemplary embodiment, a method is provided for testing whether an iontophoretic device is in an appropriate state for administering a therapeutic agent into an animal body by driving an electrotransport current through a surface of the animal body. The method includes applying a voltage across at least one electrical path leading from at least one test point and configured to lead to an electrode of the iontophoretic device, and measuring an electrical characteristic of the at least one electrical path. The method also includes determining whether the iontophoretic device is in an appropriate state for administering a therapeutic agent from the measured electrical characteristic. The measured electrical characteristic indicates that the iontophoretic device is in the appropriate state for administering the therapeutic agent into the animal body when the therapeutic agent is properly disposed with respect to the iontophoretic device. The method also includes preventing use of the iontophoretic device if the iontophoretic device is not in an appropriate state for administering the therapeutic agent into the animal body within a predetermined period of time after a first measurement of the electrical characteristic.

In accordance with another exemplary embodiment, a method is provided for testing whether an iontophoretic device is in an appropriate state for administering a therapeutic agent into an animal body by driving an electrotransport current through a surface of the animal body. The method includes applying a voltage across at least one electrical path leading from at least one test point associated with an anode and configured to lead to at least one test point associated with a cathode, and measuring an electrical characteristic of the at least one electrical path. The method includes determining whether the iontophoretic device is in an appropriate state for administering a therapeutic agent from the measured electrical characteristic. The measured electrical characteristic indicates that the iontophoretic device is in the appropriate state for administering the therapeutic agent into the animal body when the therapeutic agent is properly disposed with respect to the iontophoretic device. The method also includes preventing use of the iontophoretic device if the iontophoretic device is not in an appropriate state for administering the therapeutic agent into the animal body within a predetermined period of time after a first measurement of the electrical characteristic.

In accordance with another exemplary embodiment, a method is provided for fabricating a testing assembly for an iontophoretic device that administers a therapeutic agent into an animal body by driving an electrotransport current through a surface of the animal body. The method includes providing at least one test point in proximity to an electrode of the iontophoretic device, and providing at least one electrical path leading from the at least one test point and configured to lead to the electrode. The method also includes coupling an electrical power supply to the at least one electrical path to enable a voltage to be applied across the at least one electrical path. The method also includes programming a controller to measure an electrical characteristic of the at least one electrical path, and determine whether the iontophoretic device is in an appropriate state for administering a therapeutic agent from the measured electrical characteristic. The measured electrical characteristic indicates that the iontophoretic device is in the appropriate state for administering the therapeutic agent into the animal body when the therapeutic agent is properly disposed with respect to the iontophoretic device. The method also includes programming a controller to prevent use of the iontophoretic device if the iontophoretic device is not in an appropriate state for administering the therapeutic agent into the animal body within a predetermined period of time after a first measurement of the electrical characteristic.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 5A illustrates a top view of an exemplary electrode, and first and second electrical test points spaced from and provided in the vicinity of the electrode.

FIG. 5B illustrates a top view of the exemplary assembly of FIG. 5A, showing the outline of an exemplary conductive reservoir properly assembled with the electrode so that the reservoir establishes an electrical connection among the electrode and the first and second test points.

FIG. 5C illustrates a top view of the exemplary assembly of FIG. 5A, showing the outline of an exemplary conductive reservoir improperly assembled with the electrode so that the reservoir fails to establish an electrical connection between the electrode and the second test point and an electrical connection between the first and second test points.

FIG. 5D illustrates a top view of the exemplary assembly of FIG. 5A, showing the outline of an exemplary conductive reservoir improperly assembled with the electrode so that the reservoir fails to establish an electrical connection between the electrode and the first test point and an electrical connection between the first and second test points.

FIG. 7A illustrates a top view of an exemplary electrode, and first, second, third and fourth electrical test points spaced from and provided in the vicinity of the electrode.

FIG. 7B illustrates a top view of the exemplary assembly of FIG. 7A, showing the outline of an exemplary conductive reservoir properly assembled with the electrode so that the reservoir establishes an electrical connection between the electrode and the four test points.

FIG. 7C illustrates a top view of the exemplary assembly of FIG. 7A, showing the outline of an exemplary conductive reservoir improperly assembled with the electrode so that the reservoir fails to establish an electrical connection between the electrode and the third test point and electrical connections between the third test point and any of the other test point.

FIG. 7D illustrates a top view of the exemplary assembly of FIG. 7A, showing the outline of an exemplary conductive reservoir improperly assembled with the electrode so that the reservoir fails to establish an electrical connection between the electrode and the first or fourth test points, electrical connections between the first test point and any of the other test points, and electrical connections between the fourth test point and any of the other test points.

FIG. 9A illustrates a top view of an exemplary electrode and a ring-shaped test point spaced from and provided in the vicinity of the electrode.

FIG. 9B illustrates a top view of the exemplary assembly of FIG. 9A, showing the outline of an exemplary conductive reservoir properly assembled with the electrode so that the reservoir establishes an electrical connection between the electrode and the test point.

FIG. 9C illustrates a top view of the exemplary assembly of FIG. 9A, showing an electrical path extending between the electrode and the ring-shaped test point.

FIG. 11 is a flowchart of a generalized method of verifying the presence and alignment of one or more reservoirs relative to one or more corresponding electrodes in an iontophoretic drug delivery device.

DETAILED DESCRIPTION

Figure 1A:
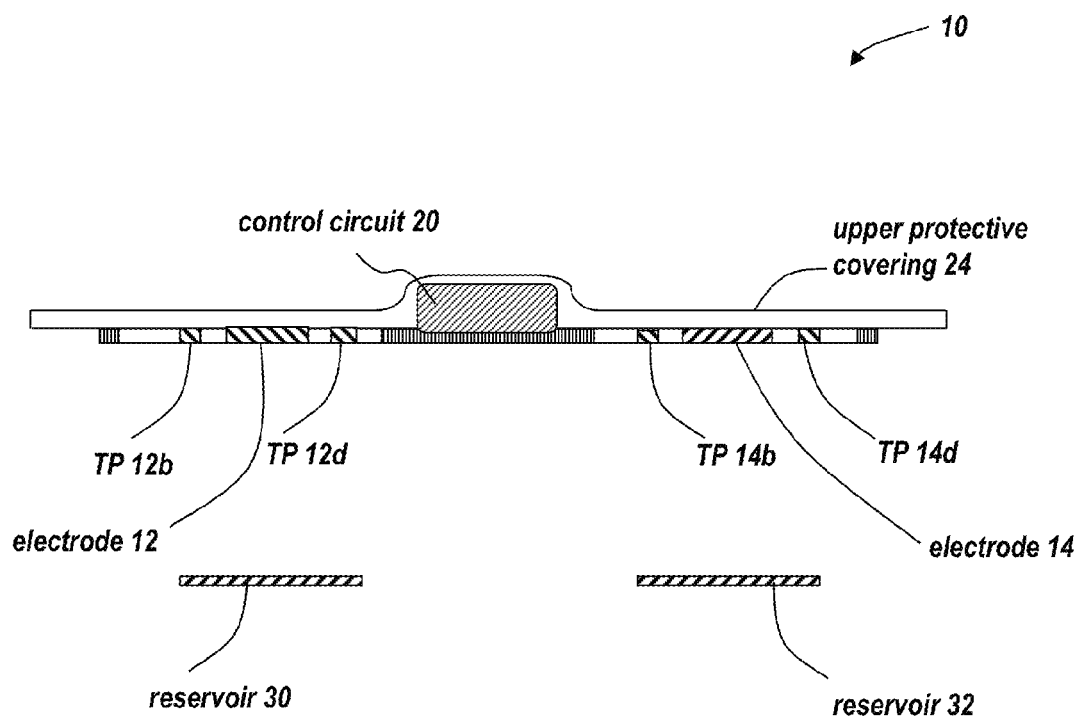
FIG. 1A illustrates a cross-sectional side view of an exemplary iontophoretic drug delivery device before assembly.

Exemplary embodiments provide testing systems, devices and methods that verify proper assembly of iontophoretic drug delivery devices. In an exemplary embodiment, a system is provided for testing whether an iontophoretic drug delivery device is in an appropriate state for administering a therapeutic agent into an animal body. An electrical characteristic of at least one electrical path associated with an electrode test point is used to determine whether the iontophoretic device is in an appropriate state. The measured electrical characteristic indicates that the iontophoretic device is in an appropriate state for administering the therapeutic agent into the animal body when the therapeutic agent is properly disposed with respect to the electrodes of the iontophoretic device.

Exemplary embodiments provide at least one electrical test point associated with an electrode in an iontophoretic therapeutic agent delivery device. Some exemplary embodiments may provide one or more electrical test points associated with an anode and one or more electrical test points associated with a cathode in an iontophoretic therapeutic agent delivery device. Upon assembly of the device, proper positioning of a conductive reservoir over an electrode in the device creates an electrical connection between the electrode and each of its one or more associated test points. In this exemplary configuration, when a conductive reservoir is not placed on a corresponding electrode, an electrical connection between the electrode and each of its one or more associated test points is non-existent or minimal. As such, detection of a non-existent or minimal electrical connection between an electrode and each of its one or more associated test points indicates that a conductive reservoir is missing from the electrode. Conversely, detection of a non-negligible electrical connection between an electrode and each of its one or more associated test points may indicate that a conductive reservoir is present and properly positioned on the electrode. On the other hand, when a conductive reservoir is present but misaligned with a corresponding electrode, the reservoir is not centered on the electrode and an electrical connection between the electrode and at least one of its one or more associated test points may be non-existent or minimal. As such, detection of a non-existent or minimal electrical connection between an electrode and at least one of its associated test points may indicate that a conductive reservoir is misaligned with the electrode. In some embodiments, detection of a non-negligible level of electrical connection between an electrode and at least one of its associated test points may indicate that a conductive reservoir is misaligned with the electrode.

Exemplary embodiments may be used to detect several inappropriate states of an assembled iontophoretic device including, but not limited to, a state in which the device has not been placed on the animal body, a state in which the device is missing one or more reservoirs, a state in which one or more reservoirs are present in the device but are misaligned relative to corresponding electrodes, and the like. Misalignment of a reservoir relative to a corresponding electrode may result if the reservoir is folded or bunched, shifted or placed off-center relative to the electrode, placed on an inappropriate electrode (e.g., if a reservoir holding a salt solution is placed on the anode, and/or if a reservoir holding a therapeutic agent in a conductive medium is placed on the cathode), and the like. Exemplary embodiments may determine these types of misalignments of one or more reservoirs relative to one or more corresponding electrodes.

Absence or misalignment of a reservoir holding a therapeutic agent in a conductive medium relative to a corresponding electrode in an iontophoretic drug delivery device may adversely affect the efficacy of the drug delivery and user experience. In a case in which a conductive reservoir is not present on a corresponding electrode, the therapeutic agent may not be administered to the user. In addition, absence of the conductive reservoir may leave the corresponding electrode exposed to the user's skin, which may cause irritation and electrochemical burning of the user's skin. In a case in which the conductive reservoirs are switched so that they are placed on the incorrect electrodes (e.g., when a reservoir simply holding a conductive medium is improperly placed on the anode and/or when a reservoir holding a therapeutic agent in a conductive medium is improperly placed on the cathode), the therapeutic agent may not be administered at all or may not be administered efficaciously. In another case in which a conductive reservoir is present but is misaligned with the corresponding electrode (e.g., leaving a portion of the electrode exposed to the user's skin), exposure of the electrode to the user's skin may cause irritation and electrochemical burning of the user's skin.

Exemplary embodiments thereby ensure correct assembly of the reservoirs relative to the electrodes, in which the reservoirs completely cover first surfaces of the electrodes facing the user's skin. Correct assembly of the reservoirs and electrodes allows delivery of an electrotransport current to efficaciously flow through the reservoirs and to reliably release the therapeutic agent from the reservoir corresponding to the anode into the user's skin. Ensuring that the electrodes are not in direct contact with the user's skin also acts as a safety feature to prevent irritation and/or accidental electrochemical burning of the user's skin during operation of the drug delivery device. Furthermore, exemplary embodiments ensure that the reservoirs are not switched so that a reservoir holding a salt solution is improperly placed on the anode and/or a reservoir holding a therapeutic agent in a conductive medium is improperly placed on the cathode. This ensures that inadvertently switched reservoirs do not result in non-efficacious dosing by the iontophoretic drug delivery device.

In an exemplary embodiment, reservoirs may be provided separately from the electrodes of an iontophoretic drug delivery device when the device is in a packaged state. A user of the device may assemble the reservoirs with the electrodes before use. In this embodiment, exemplary embodiments may verify whether the device has been properly assembled after the device is taken out of its outer packaging and before use. In another exemplary embodiment, the reservoirs may be assembled with the electrodes of an iontophoretic device before the device is placed in an outer packaging. In this embodiment, exemplary embodiments may verify whether the device has been properly assembled after fabrication of the device but before it is placed in the outer packaging.

Certain terms are defined in this section to facilitate understanding of exemplary embodiments.

The terms "user," "animal," "patient" and "subject," as used herein, refer to animals that may be treatable by drug delivery devices taught herein. Exemplary animals may include, but are not limited to, primates (e.g., humans, chimpanzees, gorillas, etc.), other mammals (e.g., cats, dogs, horses, pigs, cows, sheep, rodents, rabbits, squirrels, bears, etc.), and the like.

The terms "drug," "agent" and "therapeutic agent," as used herein, refer to any drug, agent, biologically active agent, biological substance, chemical substance or biochemical substance that is capable of being administered in a therapeutically effective amount employing drug delivery devices taught herein.

The term "iontophoresis," as used herein, refers to a technique in which an electrotransport current is used to administer a therapeutic agent transdermally to an animal body.

The terms "iontophoretic drug delivery device," "iontophoretic device," "iontophoretic drug delivery system" and "iontophoretic system," as used herein, refer to a device that employs iontophoresis to administer a therapeutic agent into an animal body using an electrotransport current. An exemplary iontophoretic device may be wearable and may be provided with coupling mechanisms (for example, Velcro™ fasteners) for attaching the device to the user's body and/or clothing.

The term "reservoir," as used herein, refers to a component in a drug delivery device for holding a conductive medium. In an exemplary embodiment, a reservoir corresponding to an anode may be configured to hold a therapeutic agent in a conductive medium, and a reservoir corresponding to a cathode may be configured to hold a conductive salt solution. Exemplary reservoirs may include, but are not limited to, a material layer, a pad, a sponge, a flexible tube or bag, a plastic matrix to hold the therapeutic agent in place, a non-conducting mesh, and the like. Some exemplary reservoirs may be pre-filled with a therapeutic agent when the drug delivery device is in the packaged state. Other exemplary reservoirs may not be pre-filled with a therapeutic agent when the drug delivery device is in the packaged state, and a user may fill the reservoirs before use.

The term "computer-readable medium," as used herein, refers to a non-transitory storage hardware, non-transitory storage device or non-transitory computer system memory that may be accessed by a controller, a microcontroller, a computational system or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM, etc.) and the like.

The terms "electrical connection" and "electrical connectivity" are used herein interchangeably to refer to a path between two or more locations or points in a drug delivery device that allows a non-negligible flow of electrons. Exemplary electrical characteristics that may be used as representing electrical connectivity include, but are not limited to, direct or indirect measures of electrical conductivity, resistance, impedance, voltage drop, current flow, capacitance, decay time after a driving signal is applied, measures proportionate to any of the above characteristics (an electrical characteristic that the proportionate to conductivity), and the like. Other exemplary electrical characteristics that may be used as representing electrical connectivity include, but are not limited to, the first and/or second time derivatives of any of the aforementioned variables.

The term "equal" is used herein, in a broad lay sense, to mean exactly equal or approximately equal within a reasonable tolerance.

The term "adjacent" is used herein, in a broad lay sense, to mean immediately adjacent or approximately adjacent within a reasonable tolerance.

Exemplary embodiments are described below with reference to the drawings. One of ordinary skill in the art will recognize that exemplary embodiments are not limited to the illustrative embodiments, and that components of exemplary systems, devices and methods are not limited to the illustrative embodiments described below.

Figure 1B:
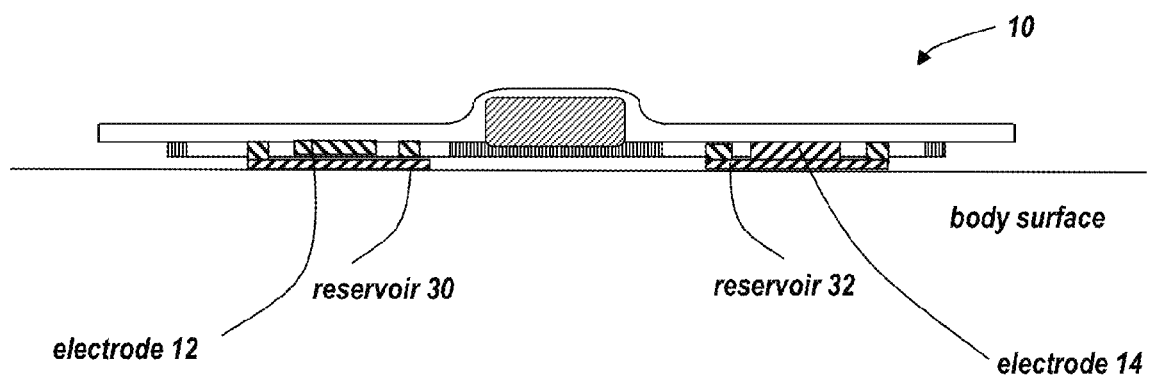
FIG. 1B illustrates a cross-sectional side view of the exemplary iontophoretic drug delivery device of FIG. 1A in an assembled state.
Figure 2:
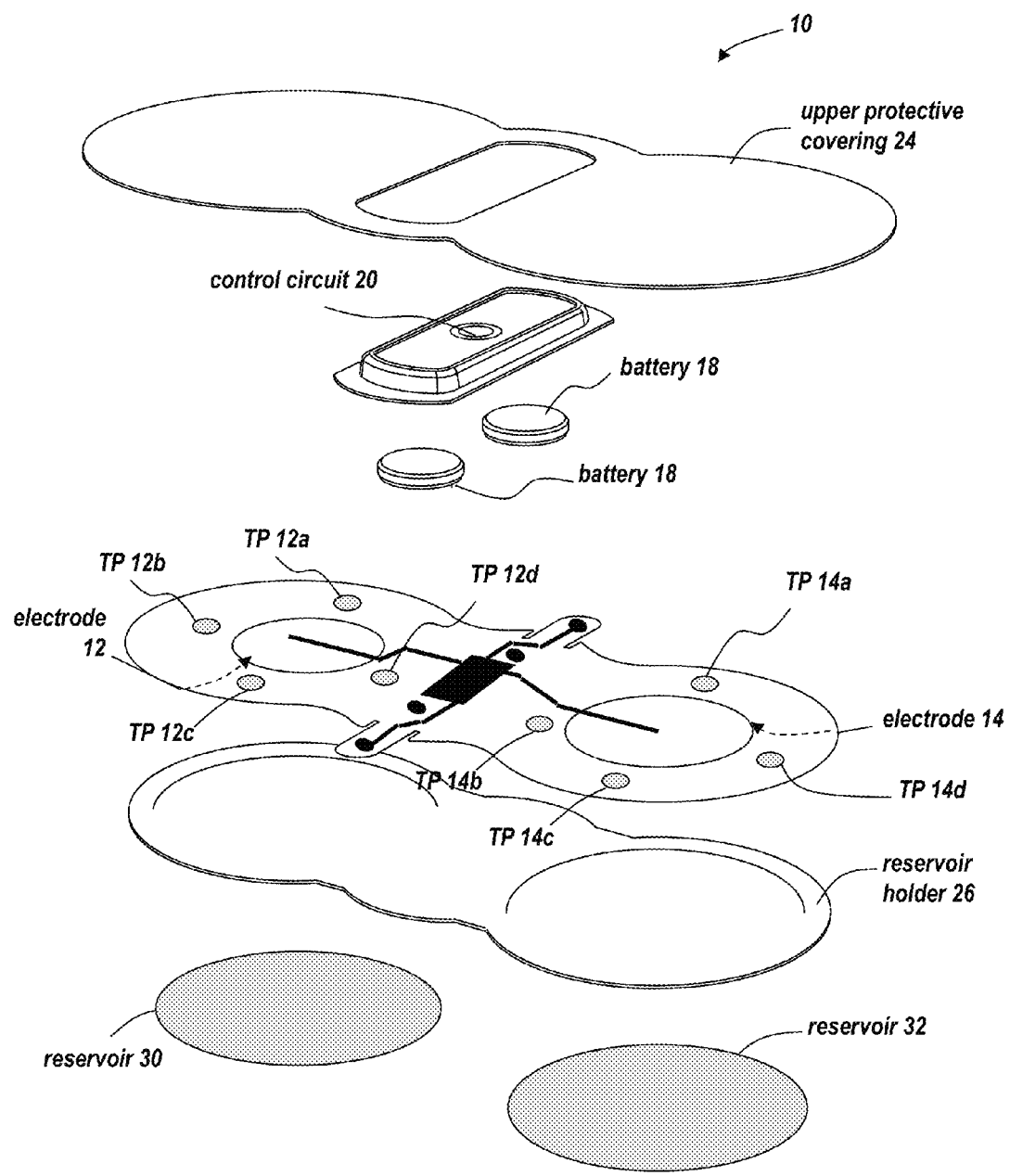
FIG. 2 illustrates an exploded perspective view of the exemplary iontophoretic drug delivery device of FIGS. 1A and 1B.

FIGS. 1A, 1B, and 2 illustrate an exemplary iontophoretic drug delivery device 10 that employs iontophoresis to transdermally deliver a therapeutic agent into a user's body. FIG. 1A illustrates a cross-sectional side view of the exemplary iontophoretic drug delivery device 10 before assembly. FIG. 1B illustrates a cross-sectional side view of the exemplary iontophoretic drug delivery device 10 of FIG. 1A in an assembled state. FIG. 2 illustrates an exploded perspective view of the exemplary iontophoretic drug delivery device 10 of FIGS. 1A and 1B. Elements of FIGS. 1A, 1B, and 2 are not drawn to scale and may not have accurate relative sizes. For example, thicknesses of some elements in FIGS. 1A, 1B, and 2 are exaggerated for illustrative purposes.

The exemplary iontophoretic drug delivery device 10 may be packaged as a patch that is applied to the skin of a user for administration of the therapeutic agent and removed from the skin of the user after administration of the therapeutic agent. Other non-patch embodiments of an iontophoretic device are also within the scope of the present invention.

The exemplary drug delivery device 10 includes one or more locations or reservoirs for holding one or more therapeutic agents. In an exemplary embodiment, a first conductive reservoir 30, associated with a first electrode, is provided for holding a conductive medium including a therapeutic agent. In an exemplary embodiment, a second conductive reservoir 32, associated with a second electrode, is provided for holding a conductive salt solution. The conductive media of the therapeutic agent and the conductive salt solution may have opposite charges. In an exemplary embodiment, the first reservoir 30 may be pre-filled in the device with the conductive media holding the therapeutic agent, and the second reservoir 32 may be pre-filled in the device with the salt solution. In another exemplary embodiment, the first reservoir 30 may not be pre-filled in the device and may be filled with the conductive media holding the therapeutic agent by a user during assembly of the device. Similarly, the second reservoir 32 may not be pre-filled in the device and may be filled with the salt solution by a user during assembly of the device.

Exemplary reservoirs may have any suitable thickness ranging from about 100 microns to about 1 inch, but are not limited to this exemplary range. In an exemplary embodiment, a drug delivery device 10 may include an optional reservoir holder 26 (see FIG. 2) to accommodate the reservoirs 30, 32 so that the reservoirs are in direct contact with the electrodes 12, 14 in the assembled state of the device. The reservoir holder 26 may take any suitable form including, but not limited to, an adhesive layer, a recessed layer sized to accommodate the reservoirs, attachment mechanisms for holding the reservoirs in place, and the like.

The exemplary drug delivery device 10 includes a first electrode 12 (e.g., a cathode or anode) and a second electrode 14 (e.g., an anode or cathode) for driving an electrotransport current into the user's skin. The first and second electrodes 12, 14 are coupled to one or more controllable power supplies 18 (see FIG. 2) that are controlled by a microcontroller to apply a potential difference across the first and second electrodes 12, 14 to drive an electrotransport current through the user's skin. The power supplies 18 may include one or more batteries in one embodiment. The first and second electrodes 12, 14 may be spaced from each other in the device 10 so that, before the device is placed on the user's body, there is a zero or minimal electrical connection across the electrodes. When the device is placed on the user's body, a direct or indirect electrical connection may be established between the electrodes via the user's body. Upon activation of the device to administer the therapeutic agent, the microcontroller controls the power supply 18 to apply a potential difference across the first and second electrodes 12, 14, which results in an electrotransport current flowing between the electrodes 12, 14 through the user's body.

Exemplary electrodes 12, 14 may have any suitable size and shape. Exemplary dimensions (e.g., lengths, widths, diameters) of the electrodes may range from about 100 microns to about 10 cm, but are not limited to this exemplary range. Exemplary cross-sectional shapes of the electrodes may include, but are not limited to, circular, oval, ring-shaped, arc-shaped, elliptical, square, rectangular, irregular, and the like. In an exemplary embodiment, the electrodes may take the form of wires coated with a suitable conductive material including, but not limited to, zinc, silver, silver/silver chloride, and the like. The electrodes may be printed on a Mylar™ substrate in an exemplary embodiment.

In an exemplary embodiment, the first and second electrodes 12, 14 may be held in place by one or more coupling mechanisms, for example, foam rings. In an exemplary embodiment, the electrodes 12, 14 may include or be covered by a polyester film. One suitable polyester film is a biaxially-oriented polyethylene terephthalate polyester film sold under the trademark Mylar™. The Mylar™ polyester film is an advantageous material because of its thinness and flexibility. In an exemplary embodiment, the polyester film of the electrodes 12, 14 may be screen-printed or etched with conductive ink including silver/silver chloride. In an exemplary embodiment, the polyester film may include a dielectric coating to provide electrical insulation. In an exemplary embodiment, one or more components of the device 10, like microprocessors and batteries, may be affixed directly onto the polyester film of the electrodes 12, 14 with glue, conductive glue, solder, or tabs. In another exemplary embodiment, the electrodes 12, 14 may comprise a polyimide film, such as Kapton™ polyimide film.

In an exemplary embodiment, the first and second reservoirs 30, 32 may be provided separately from the first and second electrodes 12, 14 when the device is in a pre-assembled packaged state. The first and second reservoirs 30, 32 may be brought into contact with the first and second electrodes 12, 14, respectively, when the device is assembled so that the first and second reservoirs 30, 32 are positioned between the skin of the user and the first and second electrodes 12, 14, respectively. In use, an electrotransport current supplied to the first electrode 12 delivers the first therapeutic agent from the first conductive reservoir 30 through a portion of the user's skin in contact with the first conductive reservoir 30. The electrotransport current may be returned to the second electrode 14 through a portion of the user's skin in contact with the second conductive reservoir 32.

Though not shown in FIG. 1B, the first and second reservoirs 30, 32 need not be the only portions of the exemplary iontophoretic drug delivery device 10 that contact the body surface. Any other portion of the device 10 that contacts the body surface should generally be non-conductive as compared to the reservoirs. For example, upper protective covering 24 may have an adhesive on the surface facing the body surface. The adhesive may contact the body surface and hold device 10 on the body surface. Similarly, other parts of device 10 may contact the body surface and possibly hold the device 10 on the body surface.

When the first and second reservoirs 30, 32 are properly positioned relative to the first and second electrodes 12, 14, the first and second reservoirs 30, 32 completely cover first surfaces of the first and second electrodes 12, 14 facing the user's skin, so that the electrodes are not exposed to or in direct contact with the user's skin. Proper assembly of the reservoirs and the electrodes in which the reservoirs completely cover the first surfaces of the electrodes, allows delivery of an electrotransport current to flow through the reservoirs and to reliably release the therapeutic agent from the reservoir corresponding to the anode into the user's skin. In addition, preventing the electrodes from being in direct contact with the user's skin prevents irritation and/or accidental electrochemical burning of the user's skin during operation of the drug delivery device.

As part of the assembly for verification of the placement and correct alignment of the reservoirs relative to the electrodes, exemplary embodiments may provide one or more electrically conductive test points associated with and provided in the vicinity of at least one of the first and second electrodes 12, 14. In some exemplary embodiments, one or more test points associated with an electrode may be spaced from the electrode. When the first and second conductive reservoirs 30, 32 are properly positioned relative to the first and second electrodes 12, 14, the first and second conductive reservoirs 30, 32 completely cover first surfaces of the electrodes. In some exemplary embodiments, the one or more test points associated with an electrode are configured so that a properly positioned reservoir will cover the electrode and its associated one or more test points and establish electrical connections among the electrode and all of its associated test points. In alternative exemplary embodiments (see FIGS. 10A through 10C for a better understanding), at least one test point associated with an electrode is configured so that a properly positioned reservoir will cover the electrode but not the at least one test point so that no electrical connection or a minimal electrical connection is established between the electrode and that at least one test point.

In the exemplary configuration in which a properly position reservoir establishes an electrical connection is established among an electrode and all of its associated test points, when a conductive reservoir is missing from a corresponding electrode, electrical connections among the electrode and each of its associated test points are non-existent or minimal. In such an exemplary configuration, detection of non-existent or minimal electrical connections among an electrode and each of its associated test points indicates that a conductive reservoir is missing on the electrode. Conversely, detection of non-negligible electrical connections among an electrode and each of its associated test points may indicate that a conductive reservoir is present and properly positioned on the electrode. On the other hand, when a conductive reservoir is present but misaligned with a corresponding electrode, an electrical connection between the electrode and at least one of its associated test points is non-existent or minimal. As such, detection of a non-existent or minimal electrical connection between an electrode and at least one of its associated test points may indicate that a conductive reservoir is misaligned with the electrode. The verification of the presence and correct positioning of a conductive reservoir relative to an electrode using exemplary test points that are configured to create an electrical connection is described in connection with FIGS. 11, 12, 13A, 13B, 14A, 14B, 15A, and 15B.

In the exemplary embodiment illustrated in FIG. 2, four exemplary electrical test points 12*a*, 12*b*, 12*c*, 12*d* are associated with the first electrode 12, although one of ordinary skill in the art will recognize that fewer or more test points may be provided in association with the first electrode. The test points 12*a*, 12*b*, 12*c*, 12*d* may be spaced from the first electrode 12 and may be arranged spacedly from one another around the first electrode 12. In an exemplary embodiment, the test points 12*a*, 12*b*, 12*c*, 12*d* may be spaced from one another and arranged around the first electrode 12 at intervals of about 90 degrees. Similarly, as illustrated in FIG. 2, four exemplary test points 14*a*, 14*b*, 14*c*, 14*d* are associated with the second electrode 14, although one of ordinary skill in the art will recognize that fewer or more test points may be provided in association with the first electrode. The test points 14*a*, 14*b*, 14*c*, 14*d* may be spaced from the second electrode 14 and may be arranged spacedly from one another around the second electrode 14. In an exemplary embodiment, the test points 14*a*, 14*b*, 14*c*, 14*d* may be spaced from one another and arranged around the second electrode 14 at intervals of about 90 degrees.

The test points associated with the first and second electrodes 12, 14 may be coupled or coupleable to a microcontroller programmed or configured to determine one or more electrical characteristics of one or more electrical paths associated with the test points. Exemplary electrical characteristics may include, but are not limited to, direct or indirect measures of conductivity, resistance, impedance, voltage drop, current flow, capacitance, decay time after a driving signal is applied, suitable measures proportionate to any of the above characteristics (for example, an electrical characteristic that is proportional or inversely proportional to conductivity), and the like. Other exemplary characteristics may include the first and/or second time derivatives of any of the aforementioned variables.

In exemplary embodiments, the first electrode 12 and/or the second electrode 14 may be associated with any suitable number of discrete electrical test points including, but not limited to, 1, 2, 3, 4, 5, 6, 7, 8, 9, 10, 11, 12, 13, 14, 15, 16, 17, 18, 19, or 20, but are not limited to this exemplary range. The number and characteristics of the test points used (e.g., size, shape, location) may be adjusted to improve the sensitivity of the verification of proper assembly of the reservoirs with the electrodes. In an exemplary embodiment, the number of test points may be increased to increase the sensitivity of the verification. In exemplary embodiments, the distance between a test point and a corresponding electrode may be adjusted to improve the sensitivity of the verification of proper assembly of the reservoirs with the electrodes. In an exemplary embodiment, increasing the distance between a test point and a corresponding electrode may improve the sensitivity of the verification of proper assembly of the reservoirs with the electrodes.

Exemplary electrical test points associated with the electrodes may have any suitable size and shape. Exemplary dimensions (e.g., lengths, widths, diameters) of the test points may range from about 10 microns to about 1 cm, but are not limited to this exemplary range. Exemplary cross-sectional shapes of the test points may include, but are not limited to, circular, oval, elliptical, arc-shaped, ring-shaped, square, rectangular, irregular, and the like. In an exemplary embodiment, the test points may take the form of wires coated with a suitable conductive material including, but not limited to, zinc, silver, silver/silver chloride, and the like. The test points may be printed on a Mylar™ substrate in an exemplary embodiment. An exemplary test point may be spaced from an associated electrode by any suitable distance ranging from about 10 microns to about 100 mm, but is not limited to this exemplary range.

The drug delivery device 10 may include one or more controllable power supplies 18 electrically coupled to the first and second electrodes 12, 14 to provide electrical energy to the electrodes. The power supply 18 may include one or more batteries in one exemplary embodiment. The drug delivery device 10 may include an exemplary electronic control circuitry 20 including or using one or more microcontrollers electrically coupled to the power supply 18, the first electrode 12 and the second electrode 14. The electronic control circuit 20 may be implementable on a flexible circuit (e.g. copper on Kapton™ polyimide film), a printed circuit board or both. The control circuit 20 may be electrically connected to one or more batteries 18, the first electrode 12 and the second electrode 14. In an exemplary embodiment, the control circuit 20 may be separable from the first and second electrodes 12 and 14. In this embodiment, the electrodes 12, 14 may be disposed after use and the control circuit 20 may be re-used. In another exemplary embodiment, the control circuit 20 may be integrally coupled to the electrodes 12, 14.

The microcontroller may be programmed or configured to control one or more aspects of the function and operation of the device 10. An exemplary microcontroller may be programmed or configured to perform one or more operations including, but not limited to, turning on/off a power supply 18, setting and/or adjusting the power supply 18, setting and/or adjusting the duration and magnitude of the current flow between the electrodes, determining one or more electrical characteristics in the device, setting and/or adjusting an operation of the device based on one or more measured electrical characteristics, providing an audio, visual or audiovisual indication of an operational state of the device to the user, and the like.

In an exemplary embodiment, the microcontroller may control the electrotransport current flowing between the first and second electrodes 12, 14 by controlling the power supply 18 using a linear regulator. In another exemplary embodiment, the microcontroller may control the electrotransport current flowing between the first and second electrodes 12, 14 by controlling the power supply 18 using a switching regulator that employs, for example, pulse width modulation (PWM), pulse frequency modulation (PFM), and the like. The current profile of the electrotransport current may not be limited to a particular shape, and may include one or more pulses, square waves, sine waves, ramps, arbitrary shapes, or any combination of waveforms, etc.

In some exemplary embodiments, the microcontroller may be programmed or configured to perform different sets of operations based on the state of the device. In an exemplary embodiment, the microcontroller may be programmed or configured to perform a first set of operations when the device is in an assembly verification state (i.e., when the device is verifying proper assembly of the first and conductive reservoirs 30, 32 with the first and second electrodes 12, 14), and a second set of subsequent operations when the device is in a drug delivery state (i.e., when the device is administering the therapeutic agent to a user's body).

The drug delivery system 10 may include a circuitry layer including the first electrode 12 (e.g., an anode or a cathode), a second electrode 14 (e.g., a cathode or an anode), and one or more test points associated with the first and second electrodes (e.g., test points 12a, 12b, 12c, 12d associated with the first electrode 12 and test points 14a, 14b, 14c, 14d associated with the second electrode 14). The circuitry layer may also include the control circuit 20 coupled to the electrodes and the test points. The drug delivery system 10 may include an upper protective covering 24 to cover and protect the upper portion of the circuitry layer and to prevent direct contact of a user's skin with the circuitry layer.

FIGS. 1A, 1B, and 2 illustrate exemplary embodiments of a drug delivery system (i.e., a "patch") having a certain packaging configuration. Other exemplary embodiments of a drug delivery system as taught herein may have different packaging configurations as taught, for example, in U.S. Pat. No. 6,745,071, titled "Iontophoretic Drug Delivery System," issued Jun. 1, 2004, and U.S. Pat. No. 7,973,058, titled "Transdermal Methods and Systems for the Delivery of Anti-Migraine Compounds," issued Jul. 5, 2011. The entire contents of each of the above-referenced patents are expressly incorporated herein in their entirety by reference.

Figure 3:
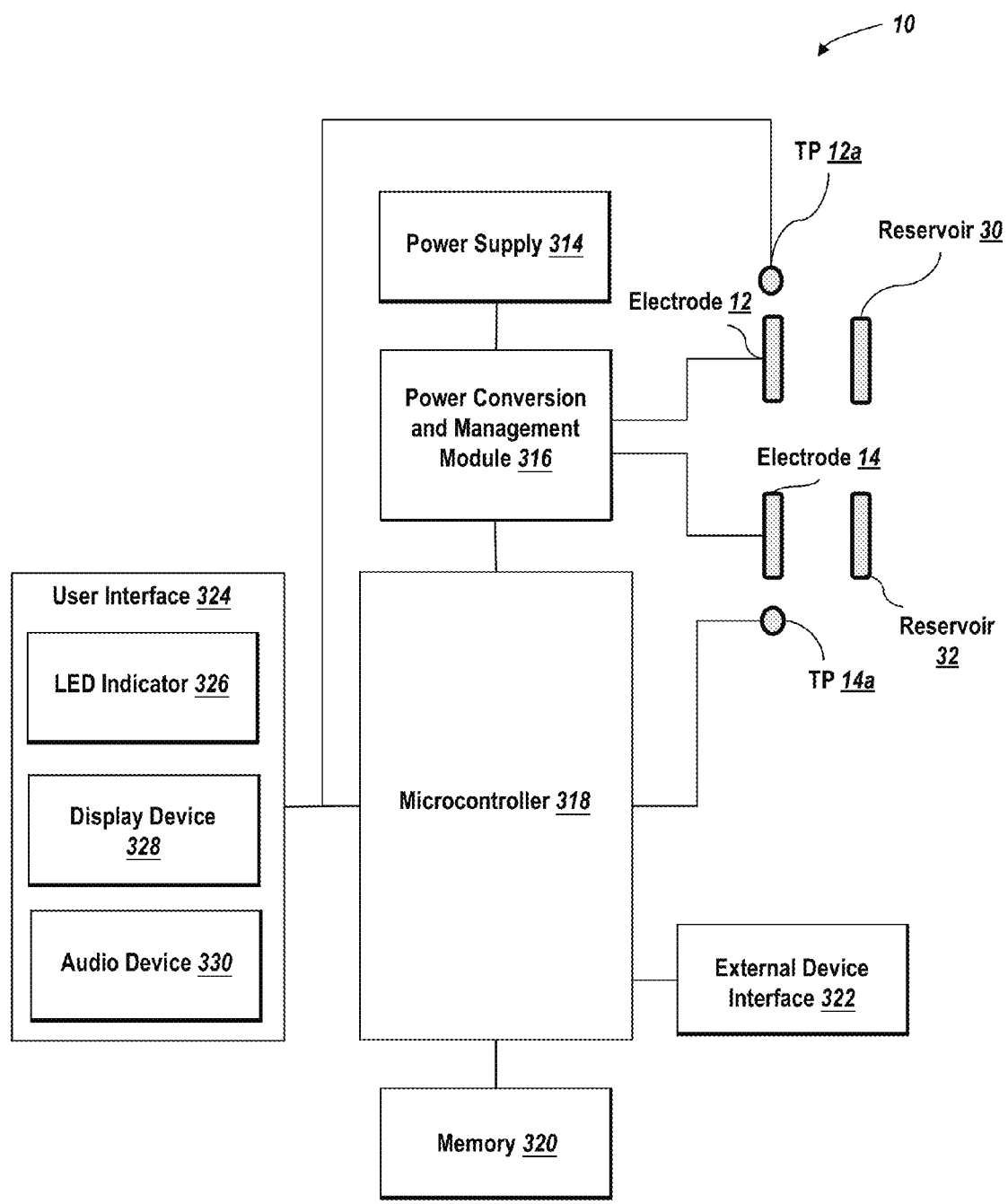
FIG. 3 illustrates a block diagram of exemplary components of an exemplary iontophoretic drug delivery device.

FIG. 3 illustrates a block diagram of certain exemplary components of the exemplary iontophoretic drug delivery device 10. The drug delivery device 10 may include an anode 12, and one or more anode test points 12a provided in the vicinity of the anode 12. The drug delivery device 10 may include a cathode 14, and one or more cathode test points 14a provided in the vicinity of the cathode 14. A first reservoir 30 may be pre-assembled with the anode 12 in the device, or may be provided separately from the anode 12 for assembly by a user before use. When properly assembled with the anode 12, the first reservoir 30 may be disposed between the anode 12 and the user's skin so that the first reservoir 30 completely covers first surfaces of the anode 12 and the anode test point 12a facing the user's skin. In an exemplary embodiment, the first reservoir 30 may contain or hold a therapeutic agent in a conductive medium. A second reservoir 32 may be pre-assembled with the cathode 14 in the device, or may be provided separately from the cathode 14 for assembly by a user before use. When properly assembled with the cathode 14, the second reservoir 32 may be disposed between the cathode 14 and the user's skin so that the second reservoir 32 completely covers first surfaces of the cathode 14 and the cathode test point 14a facing the user's skin. In an exemplary embodiment, the second reservoir 32 may contain or hold a salt solution.

The drug delivery device 10 may include a controllable power supply 314 for supplying electrical energy to the electrodes 12, 14. The power supply 314 may be electrically coupled to a power conversion and management module 316 that is programmed or configured to control one or more aspects of the power supply 314 so that the electrical energy delivered to the electrodes 12, 14 is suitable for the operation of the device 10. The power conversion and management module 316 may be electrically coupled to a microcontroller 318 programmed or configured to perform one or more operations including, but not limited to, controlling the operation of the power supply 314, controlling the power conversion and management module 316, determining one or more electrical characteristics associated with the electrodes 12, 14, determining one or more electrical characteristics associated with the test points 12a, 14a, and the like.

In an exemplary embodiment, the microcontroller 318 may be electrically coupled to a volatile or non-volatile memory 320, for example, flash memory, electrically erasable programmable read-only memory (EEPROM), RAM, SRAM, DRAM, and the like. The memory 320 may store information on any aspect of its operation including, but not limited to, one or more electrical characteristics associated with the electrodes 12, 14, one or more electrical characteristics associated with the test points 12a, 14a, time spent in a testing mode, and the like.

In an exemplary embodiment, the microcontroller 318 may be electrically coupled to an interface to an external device interface 322, for example, a serial port that may be coupled to a PC. The microcontroller 318 may receive information and/or instructions via the interface 322, for example, one or more computer-executable instructions for programming the microcontroller 318. In an exemplary embodiment, the computer-executable instructions for programming the microcontroller may be stored or encoded on one or more non-transitory computer-readable media that may be interfaced with the microcontroller 318 at interface 322. The microcontroller 318 may, in some exemplary embodiments, transmit information on any aspect of its operation to an external computing or monitoring device via the interface 322.

The drug delivery device 10 may include a machine-human interface 324 to provide information to the user during its operation. In an exemplary embodiment, the interface 324 may include an LED indicator light 326 that is in an off state when the device is not dosing, flashes when the device is in a testing mode, and is in a solid on state when the device is dosing. In an exemplary embodiment, the interface 324 may include a display device 328 to display any suitable information to the user, for example, a textual or pictorial warning that the reservoirs 30, 32 have not been properly assembled with the electrodes 12, 14. In an exemplary embodiment, the interface 324 may include an audio device 330 to provide an audio warning that the reservoirs 30, 32 have not been properly assembled with the electrodes 12, 14. The machine-human interface 324 may be electrically coupled to the microcontroller 318 to allow the microcontroller 318 to control the operation of the interface 324.

One of ordinary skill in the art will recognize that the drug delivery device 10 may include more or fewer components than those shown in FIG. 3.

FIGS. 4-10 illustrate certain exemplary configurations of electrical test points associated with an electrode, provided in accordance with exemplary embodiments. The exemplary configurations of FIGS. 4-10 may be used to detect misalignment of a reservoir relative to a corresponding electrode including, but not limited to, a reservoir that is folded or bunched, shifted or placed off-center relative to the electrode, placed on an inappropriate electrode (e.g., if a reservoir holding a salt solution is placed on the anode, and/or if a reservoir holding a therapeutic agent in a conductive medium is placed on the cathode), is missing from an electrode, and the like.

Figure 4A:
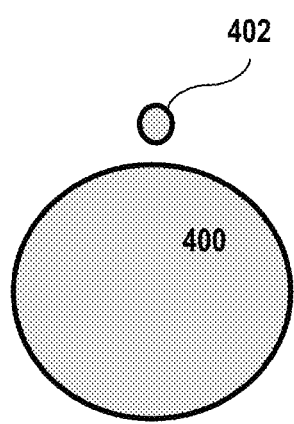
FIG. 4A illustrates a top view of an exemplary electrode and an electrical test point spaced from and provided in the vicinity of the electrode.
Figure 4B:
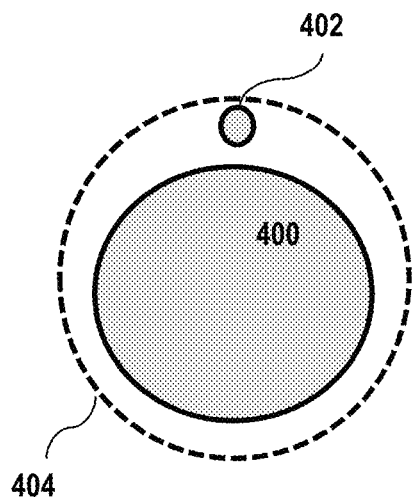
FIG. 4B illustrates a top view of the exemplary assembly of FIG. 4A, showing the outline of an exemplary conductive reservoir properly assembled with the electrode so that the reservoir establishes an electrical connection between the electrode and the test point.
Figure 4C:
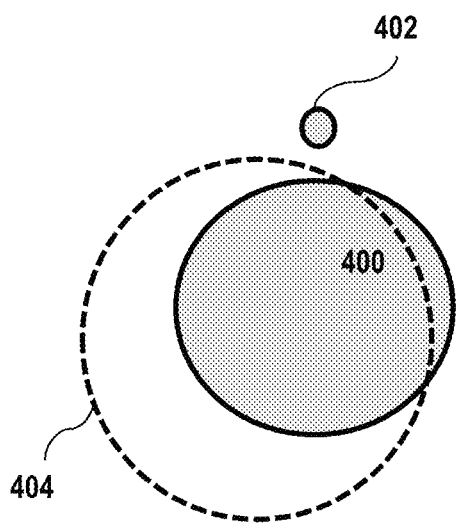
FIG. 4C illustrates a top view of the exemplary assembly of FIG. 4A, showing the outline of an exemplary conductive reservoir improperly assembled with the electrode so that the reservoir fails to establish an electrical connection between the electrode and the test point.

FIG. 4A illustrates a top view of an exemplary electrode 400 and a test point 402 spaced from and provided in the vicinity of the electrode 400. FIG. 4B illustrates a top view of the exemplary assembly of FIG. 4A, showing the outline of an exemplary conductive reservoir 404 properly assembled with the electrode 400 so that the reservoir 404 establishes an electrical connection between the electrode 400 and the test point 402. FIG. 4C illustrates a top view of the exemplary assembly of FIG. 4A, showing the outline of an exemplary conductive reservoir 404 improperly assembled with the electrode 400 so that the reservoir 404 fails to establish an electrical connection between the electrode 400 and the test point 402 and an electrical connection between the test points 402, 404. As such, detection of a non-existent or minimal electrical connection between the electrode 400 and the test point 402 indicates incorrect positioning of the conductive reservoir 404 relative to the electrode 400.

FIG. 5A illustrates a top view of an exemplary electrode 500, and a first test point 502a and a second test point 502b spaced from and provided in the vicinity of the electrode 500. Exemplary test points 502a, 502b are spaced from each other by about 180 degrees. FIG. 5B illustrates a top view of the exemplary assembly of FIG. 5A, showing the outline of an exemplary conductive reservoir 504 properly assembled with the electrode 500 so that the reservoir 504 establishes an electrical connection among the electrode 500, the first test point 502a and the second test point 502b. As such, detection of a non-negligible electrical connection among the electrode 500, the first test point 502a and the second test point 502b indicates correct positioning of the conductive reservoir 504 relative to the electrode 500.

FIG. 5C illustrates a top view of the exemplary assembly of FIG. 5A, showing the outline of an exemplary conductive reservoir 504 improperly assembled with the electrode 500 so that the reservoir 504 fails to establish an electrical connection between the electrode 500 and the second test point 502b or between the test points 502a, 502b. As such, detection of a non-existent or minimal electrical connection between the electrode 500 and the second test point 502b indicates incorrect positioning of the conductive reservoir 504 relative to the electrode 500.

FIG. 5D illustrates a top view of the exemplary assembly of FIG. 5A, showing the outline of an exemplary conductive reservoir 504 improperly assembled with the electrode 500 so that the reservoir 504 fails to establish an electrical connection between the electrode 500 and the first test point 502a or between the test points 502a, 502b. As such, detection of a non-existent or minimal electrical connection between the electrode 500 and the first test point 502a indicates incorrect positioning of the conductive reservoir 504 relative to the electrode 500.

Figure 6A:
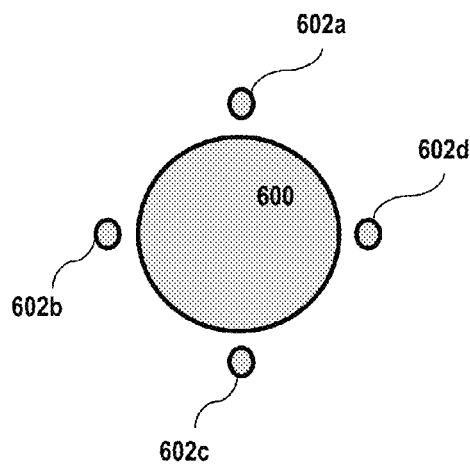
FIG. 6A illustrates a top view of an exemplary electrode, and first, second, third and fourth electrical test points spaced from and provided in the vicinity of the electrode.
Figure 6B:
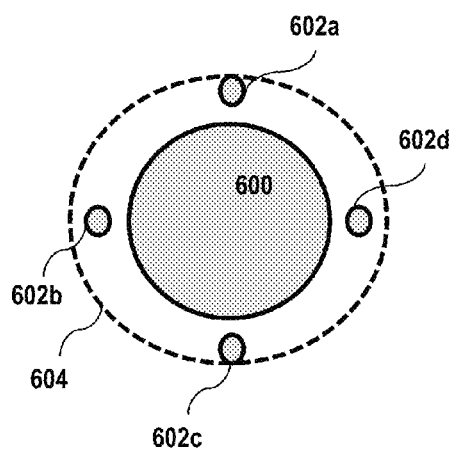
FIG. 6B illustrates a top view of the exemplary assembly of FIG. 6A, showing the outline of an exemplary conductive reservoir properly assembled with the electrode so that the reservoir establishes an electrical connection among the electrode and the four test points.

FIG. 6A illustrates a top view of an exemplary electrode 600, and a first test point 602a, a second test point 602b, a third test point 602c, and a fourth test point 602d spaced from and provided in the vicinity of the electrode 600. Exemplary test points 602a, 602b, 602c, 602d are spaced from one another around the electrode at intervals of about 90 degrees. FIG. 6B illustrates a top view of the exemplary assembly of FIG. 6A, showing the outline of an exemplary conductive reservoir 604 properly assembled with the electrode 600 so that the reservoir 604 establishes an electrical connection among the electrode 600, the first test point 602a, the second test point 602b, the third test point 602c, and the fourth test point 602d. As such, detection of a non-negligible electrical connection among the electrode 600, the first test point 602a, the second test point 602b, the third test point 602c, and the fourth test point 602d indicates correct positioning of the conductive reservoir 604 relative to the electrode 600.

Figure 6C:
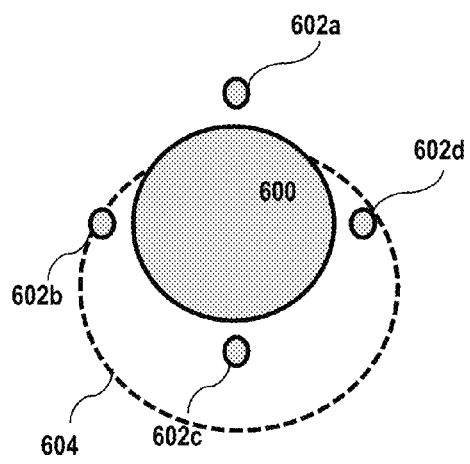
FIG. 6C illustrates a top view of the exemplary assembly of FIG. 6A, showing the outline of an exemplary conductive reservoir improperly assembled with the electrode so that the reservoir fails to establish an electrical connection between the electrode and the third test point and electrical connections between the third test point and any of the other test points.

FIG. 6C illustrates a top view of the exemplary assembly of FIG. 6A, showing the outline of an exemplary conductive reservoir 604 improperly assembled with the electrode 600 so that the reservoir 604 fails to establish an electrical connection between the electrode 600 and the first test point 602a or between the first test point 602a and any of the other test points. As such, detection of a non-existent or minimal electrical connection between the electrode 600 and the first test point 602a indicates incorrect positioning of the conductive reservoir 604 relative to the electrode 600.

Figure 6D:
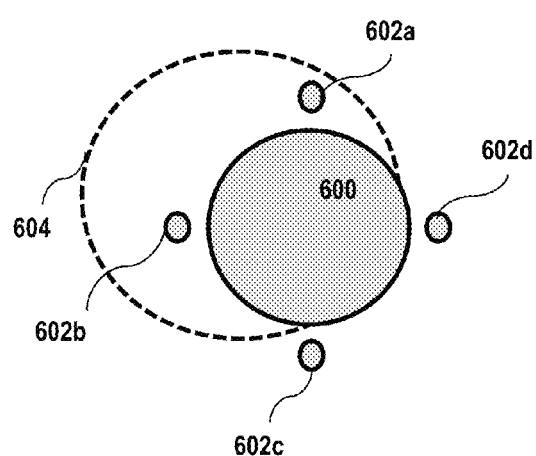
FIG. 6D illustrates a top view of the exemplary assembly of FIG. 6A, showing the outline of an exemplary conductive reservoir improperly assembled with the electrode so that the reservoir fails to establish an electrical connection between the electrode and the third or fourth test points, electrical connections between the third test point and any of the other test points, and electrical connections between the fourth test point and any of the other test points.

FIG. 6D illustrates a top view of the exemplary assembly of FIG. 6A, showing the outline of an exemplary conductive reservoir 604 improperly assembled with the electrode 600 so that the reservoir 604 fails to establish an electrical connection among the electrode 600, the third test point 602c and the fourth test point 602d. As such, detection of a non-existent or minimal electrical connection among the electrode 600, the third test point 602c and the fourth test point 602d indicates incorrect positioning of the conductive reservoir 604 relative to the electrode 600.

FIG. 7A illustrates a top view of an exemplary electrode 700, and a first test point 702a, a second test point 702b, a third test point 702c and a fourth test point 702d spaced from and provided in the vicinity of the electrode 700. The exemplary test points may be configured in discrete arc-shaped structures that are arranged at intervals around the electrode 700. Exemplary test points 702a, 702b, 702c, 702d may be arranged at intervals of about 90 degrees from one another. FIG. 7B illustrates a top view of the exemplary assembly of FIG. 7A, showing the outline of an exemplary conductive reservoir 704 properly assembled with the electrode 700 so that the reservoir 704 establishes an electrical connection among the electrode 700, the first test point 702a, the second test point 702b, the third test point 702c and the fourth test point 702d. As such, detection of a non-negligible electrical connection among the electrode 702, the first test point 702a, the second test point 702b, the third test point 702c and the fourth test point 702d indicates correct positioning of the conductive reservoir 704 relative to the electrode 700.

FIG. 7C illustrates a top view of the exemplary assembly of FIG. 7A, showing the outline of an exemplary conductive reservoir 704 improperly assembled with the electrode 700 so that the reservoir 704 fails to establish an electrical connection between the electrode 700 and the third test point 702c or between the third test point 702c and any of the other test points. As such, detection of a non-existent or minimal electrical connection between the electrode 700 and the third test point 702c indicates incorrect positioning of the conductive reservoir 704 relative to the electrode 700.

FIG. 7D illustrates a top view of the exemplary assembly of FIG. 7A, showing the outline of an exemplary conductive reservoir 704 improperly assembled with the electrode 700 so that the reservoir 704 fails to establish an electrical connection among the electrode 700, the first test point 702a and the fourth test point 702d. As such, detection of a non-existent or minimal electrical connection among the electrode 700, the first test point 702a and the fourth test point 702d indicates incorrect positioning of the conductive reservoir 704 relative to the electrode 700.

In order to determine the electrical connectivity of an electrical path in the device, the microcontroller may instruct the power supply of the device to transmit a suitable electrical signal to the electrodes. Any suitable electrical signal may be used including one or more pulses or waves. An exemplary electrical signal may have a single constant value, alternative positive and negative values where magnitude and frequency may be predefined, and the like. The characteristics of the electrical signal (e.g., magnitude, signal shape, signal magnitude, duty cycle, frequency, etc.) may be predefined and/or controlled. An exemplary electrical signal may be a square pulse or wave having a voltage ranging from about 1 V to about 5 V and lasting for about 10 microseconds to about 5 milliseconds. In an exemplary embodiment, the pulse duration of a pulsed signal may be modulated to minimize cross-talk between measurements. The microcontroller may then detect a measure of electrical connectivity along at least one electrical path associated with a test point provided in the device. Some exemplary electrical paths along which electrical connectivity may be detected are described with reference to FIGS. 8A-8E, 9A-9C, 10A-10D, and 16.

Figure 8A:
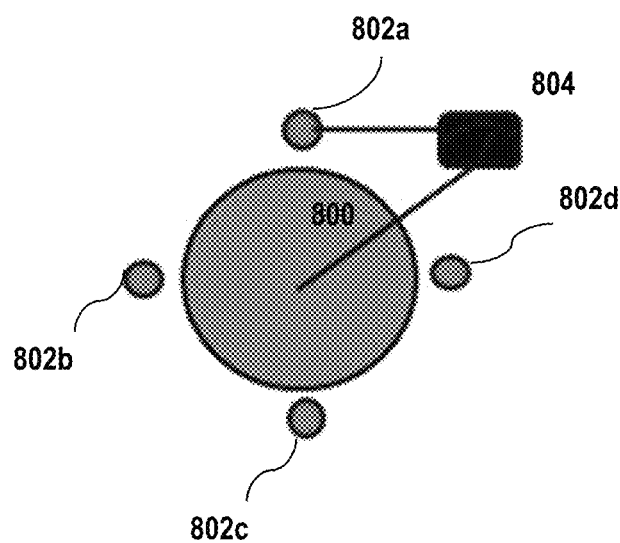
FIG. 8A illustrates an electrical path extending between an electrode and a test point for determining one or more electrical characteristics of the electrical path.
Figure 8B:
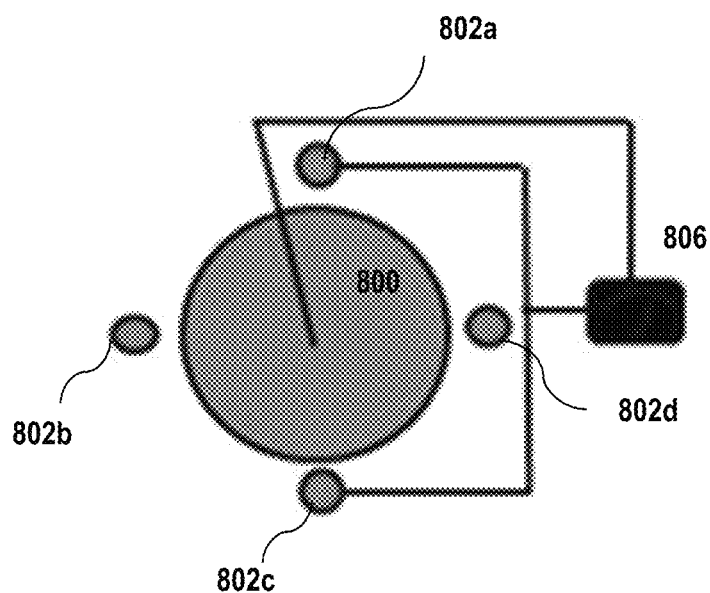
FIG. 8B illustrates an electrical path extending between an electrode and a tied connection between two opposite test points for determining one or more electrical characteristics of the electrical path.
Figure 8C:
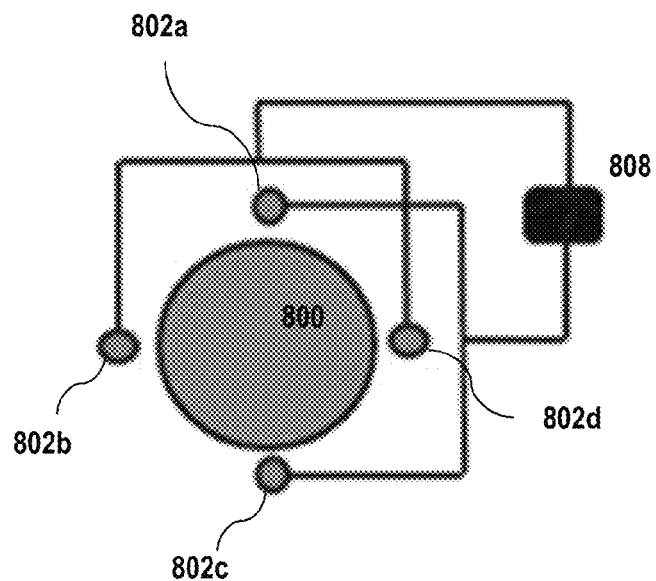
FIG. 8C illustrates an electrical path extending between a tied connection between two opposite test points and a tied connection between two opposite test points for determining one or more electrical characteristics of the electrical path.
Figure 8D:
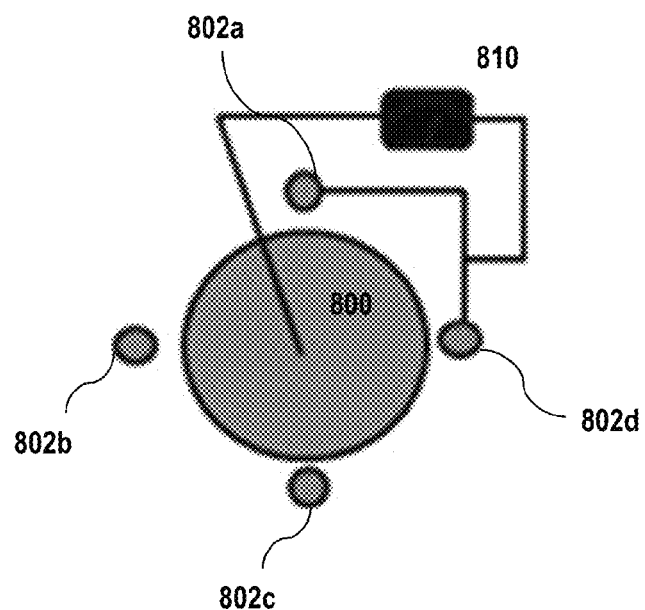
FIG. 8D illustrates an electrical path extending between an electrode and a tied connection between two adjacent test points for determining one or more electrical characteristics of the electrical path.
Figure 8E:
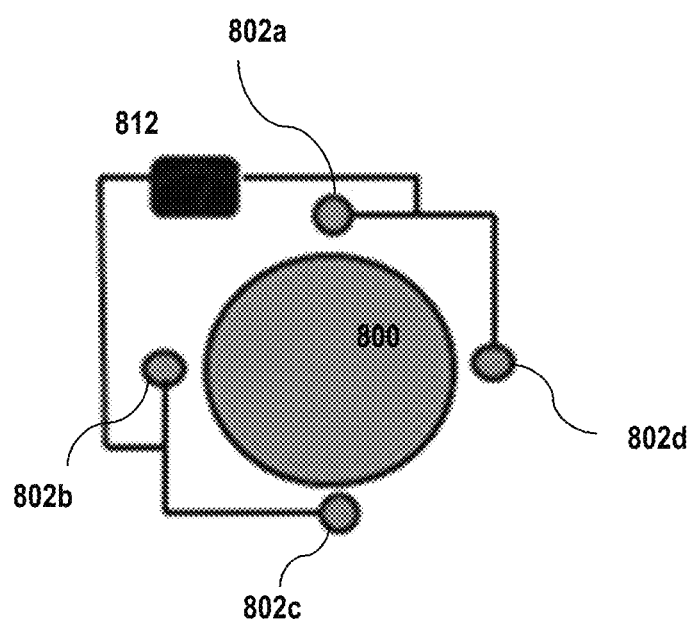
FIG. 8E illustrates an electrical path extending between a tied connection between two adjacent test points and a tied connection between two adjacent test points for determining one or more electrical characteristics of the electrical path.

FIGS. 8A-8E illustrate an electrode 800 and four associated test points 802a, 802b, 802c, 802d, showing different exemplary electrical paths among two or more components at which one or more electrical characteristics may be determined to detect proper positioning of a reservoir (not pictured) with the electrode 800. As illustrated in FIG. 8A, one or more electrical characteristics may be determined along electrical path 804 extending between the electrode 800 and the test point 802a. As illustrated in FIG. 8B, one or more electrical characteristics may be determined along electrical path 806 extending between the electrode 800 and a tied connection between opposite test points 802a and 802c. As illustrated in FIG. 8C, one or more electrical characteristics may be determined along electrical path 808 extending between a tied connection between opposite test points 802a, 802c and a tied connection between opposite test points 802b, 802d. As illustrated in FIG. 8D, one or more electrical characteristics may be determined along electrical path 810 extending between the electrode 800 and a tied connection between adjacent test points 802a and 802d. As illustrated in FIG. 8E, one or more electrical characteristics may be determined along electrical path 812 extending between a tied connection between adjacent test points 802a, 802d and a tied connection between adjacent test points 802b, 802c. Detection of a non-existent or minimal electrical connection along one or more of the electrical paths shown in FIGS. 8A-8E may indicate that a reservoir is either not present in the device or is misaligned with the electrode so that the part or the entire first surface of the electrode is exposed to the user's skin.

One of ordinary skill in the art will recognize that other electrical paths may be used to determine the electrical connectivity between an electrode and one or more of its associated test points. For example, an electrical path may be used between a first set of one or more test points associated with an electrode and a second set of one or more test points associated with the electrode.

FIGS. 9 and 10 illustrate exemplary ring-shaped configurations of electrical test points associated with an electrode. FIG. 9A illustrates a top view of an exemplary electrode 900 and a ring-shaped test point 902 spaced from and encircling the electrode 900. As illustrated in 9A, absence of a conductive reservoir on the electrode 900 results in a non-existent or minimal electrical connection between the electrode 900 and the test point 902. As such, detection of a non-existent or minimal electrical connection between the electrode 900 and the test point 902 indicates an absence of a conductive reservoir on the electrode 900.

FIG. 9B illustrates a top view of the exemplary assembly of FIG. 9A, showing the outline of an exemplary conductive reservoir 904 properly assembled with the electrode 900 so that the reservoir 904 establishes an electrical connection between the electrode 900 and the test point 902. Detection of a non-negligible electrical connection between the electrode 900 and the test point 902 indicates presence of a conductive reservoir 904 on the electrode 900.

FIG. 9C illustrates a top view of the exemplary assembly of FIG. 9A, showing an electrical path 906 extending between the electrode 900 and the test point 902 that may be used to detect whether a non-negligible electrical connection is established between the electrode 900 and the test point 902 by, for example, a properly positioned reservoir.

Figure 10A:
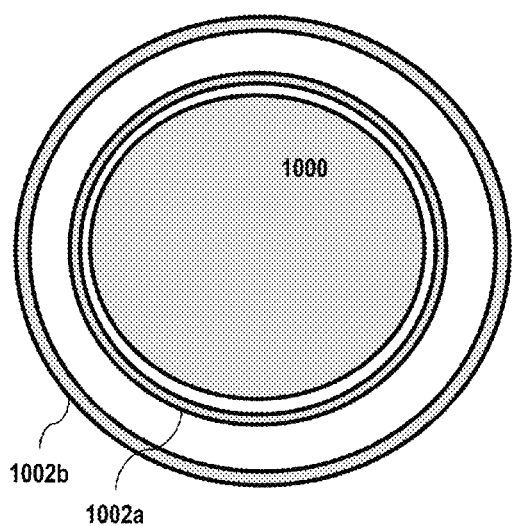
FIG. 10A illustrates a top view of an exemplary electrode, a first ring-shaped test point and a second ring-shaped test point spaced from and provided in the vicinity of the electrode.

FIG. 10A illustrates a top view of an exemplary electrode 1000, a first ring-shaped test point 1002a and a second ring-shaped test point 1002b spaced from and encircling the electrode 1000. The second ring-shaped test point 1002b may have a larger inner diameter than the outer diameter of the first ring-shaped test point 1002a. The second ring-shaped test point 1002b may encircle the first ring-shaped test point 1002a and may be spaced from the first ring-shaped test point 1002a. As illustrated in 10A, absence of a conductive reservoir on the electrode 1000 results in a non-existent or minimal electrical connection between the electrode 1000 and the first test point 1002a. As such, detection of a non-existent or minimal electrical connection between the electrode 1000 and the first test point 1002a indicates an absence of a conductive reservoir on the electrode 1000.

Figure 10B:
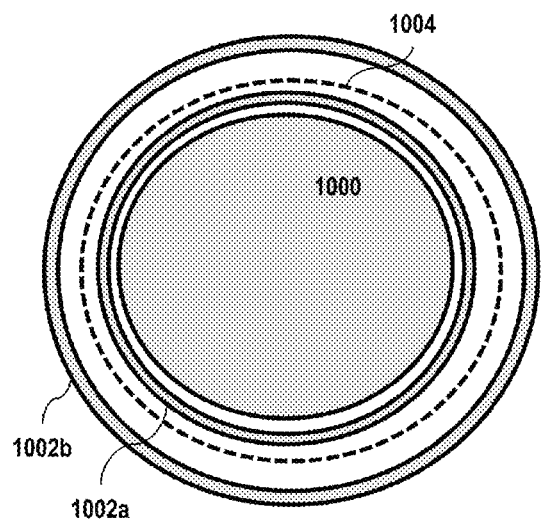
FIG. 10B illustrates a top view of the exemplary assembly of FIG. 10A, showing the outline of an exemplary conductive reservoir properly assembled with the electrode so that the reservoir establishes an electrical connection between the electrode and the closer test point and does not establish an electrical connection between the electrode and the farther test point or between the two test points.

FIG. 10B illustrates a top view of the exemplary assembly of FIG. 10A, showing the outline of an exemplary conductive reservoir 1004 properly assembled with the electrode 1000 so that the reservoir 1004 establishes an electrical connection between the electrode 1000 and the first test point 1002a. At the same time, correct positioning of the conductive reservoir 1004 on the electrode 1000 results in non-existent or minimal electrical connections between the electrode 1000 and the second test point 1002b and between the first test point 1002a and the second test point 1002b. As such, detection of a non-negligible electrical connection between the electrode 1000 and the first test point 1002a, and detection of a non-existent or minimal electrical connection between the first test point 1002a and the second test point 1002b, indicates correct positioning of a conductive reservoir 1004 on the electrode 1000. Similarly, detection of a non-negligible electrical connection between the electrode 1000 and the first test point 1002a, and detection of a non-existent or minimal electrical connection between the electrode 1000 and the second test point 1002b, indicates correct positioning of a conductive reservoir 1004 on the electrode 1000.

Figure 10C:
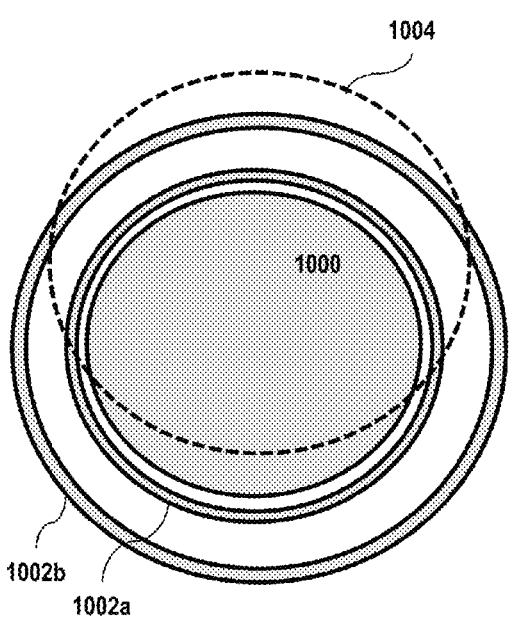
FIG. 10C illustrates a top view of the exemplary assembly of FIG. 10A, showing the outline of an exemplary conductive reservoir improperly assembled with the electrode so that the reservoir establishes an electrical connection between two test points.

FIG. 10C illustrates a top view of the exemplary assembly of FIG. 10A, showing the outline of an exemplary conductive reservoir 1004 improperly assembled with the electrode 1000 so that the reservoir 1004 establishes an electrical connection between the first test point 1002a and the second test point 1002b. As such, detection of a non-negligible electrical connection between the first test point 1002a and the second test point 1002b indicates incorrect positioning of the conductive reservoir 1004 relative to the electrode 1000.

Figure 10D:
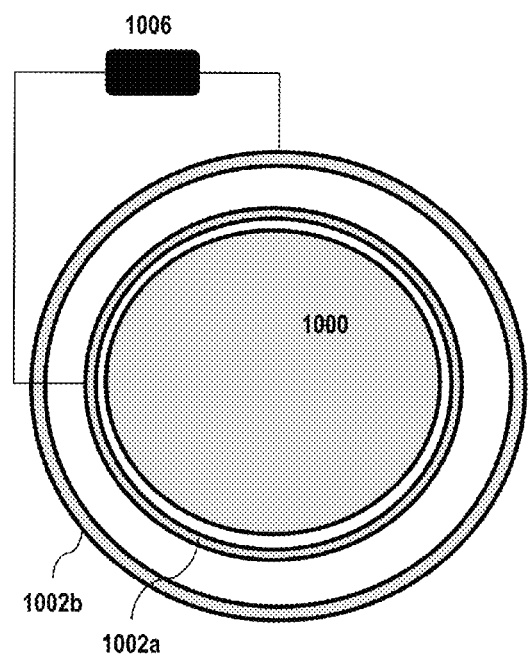
FIG. 10D illustrates a top view of the exemplary assembly of FIG. 10A, showing an electrical path extending between the first and second ring-shaped test points.

FIG. 10D illustrates a top view of the exemplary assembly of FIG. 10A, showing an electrical path 1006 extending between the first test point 1002a and the second test point 1002b that may be used to detect whether a non-negligible electrical connection is established between the two test points by, for example, an improperly positioned reservoir.

Figure 16:
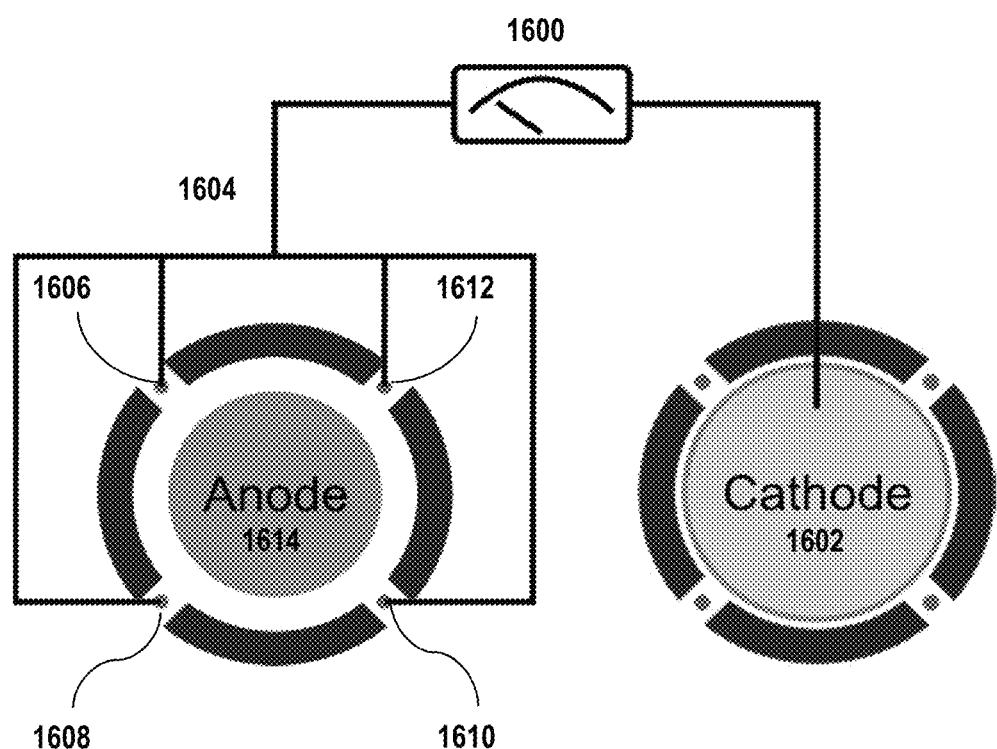
FIG. 16 illustrates a top view of an exemplary anode and an exemplary cathode, showing an electrical path extending across the anode and the cathode for detecting an electrical connectivity across the electrodes.

FIG. 16 illustrates a top view of an exemplary anode 1614 and an exemplary cathode 1602, showing an electrical path 1600 extending across the anode and the cathode for detecting an electrical connectivity across the electrodes. In this exemplary electrical path 1600, an electrical connection is established between the cathode 1602 and a tied connection 1604 of all of the test points 1606, 1608, 1610, 1612 associated with the anode 1614. One of ordinary skill in the art will recognize that other electrical paths may be used to determine the electrical connectivity across the electrodes. In one example, an electrical path may be used between the anode 1614 and one or more cathode test points. In another example, an electrical path may be used between the anode 1614 and the cathode 1602.

FIG. 11 is a flowchart of a generalized method 1100 of verifying the presence and alignment of one or more reservoirs relative to one or more corresponding electrodes in an iontophoretic drug delivery device. Upon manufacture of the device, the variables used by the microcontroller of the device are initialized before the device is made available for use. In an exemplary embodiment, the stored variable values may be output, for example, on a display device or as a printout.

As indicated in FIG. 11, the device is in an energy saving state before assembly by a user. In the energy saving state, the circuitry and microcontroller outputs in the device are turned off, and the device is polled to activate the microcontroller at a predetermined time interval in order to save energy. In an exemplary embodiment, the microcontroller may poll the device or generate an interrupt at regular intervals. Exemplary polling intervals may range from about 0.1 seconds to about 60 seconds, but are not limited to this exemplary range. An exemplary polling interval may be about 1 second.

When the microcontroller is activated periodically in the energy saving state upon polling, the device enters Stage 1 represented as step 1104. Upon polling in step 1104 (Stage 1), the microcontroller determines if the device is being assembled, for example, by positioning of the reservoirs over the electrodes and associated test points. Further details of Stage 1 are described herein with reference to FIG. 12. If it is determined that the device is not being assembled, the method returns to the energy saving state in step 1106. If, on the other hand, it is determined that the device is being assembled, the method proceeds to Stage 2 represented as step 1108.

Upon polling in step 1108 (Stage 2), the microcontroller determines if the device is being assembled properly. Further details of Stage 2 are described herein with reference to FIGS. 13A and 13B. If it is determined that the device is being assembled properly, the method proceeds to Stage 3 represented as step 1112. If it is determined that the device is not being assembled properly, the method may repeat step 1108 upon polling. If the device remains in testing step 1108 for a cumulative time period that exceeds a predetermined cumulative testing time limit, then the device is deactivated in step 1110. This time check may be performed each time the device is polled. Deactivation of a device that spends too long in the testing mode is advantageous in preventing the device from delivering a therapeutically ineffective dose of the therapeutic agent. If the device spends too much time in the assembly detection mode, this is likely to drain the power supply of the device and to dry out the reservoirs. Administration of a therapeutic agent using a device with a drained power supply is risky because the device may be unable to administer a therapeutically effective dose. In addition, deactivation of a device that spends too long in the testing mode is advantageous because such a device may have serious defects. An exemplary cumulative testing time limit may range from about five minutes to about thirty minutes, but is not limited to this exemplary range.

Upon polling in step 1112 (Stage 3), the microcontroller determines if the user's body is detected at the device, i.e., if the device is placed on the user's body. If it is determined that the device is placed on the user's body, the method proceeds to Stage 4 represented as step 1116. If it is determined that the device is not placed on the user's body, the method may repeat step 1112 upon polling. If the device remains in testing steps 1108 and/or 1112 for a cumulative time period that exceeds the cumulative testing time limit, then the device is deactivated in step 1114.

Upon polling in step 1116 (Stage 4), the microcontroller determines if the device is assembled properly on the user's body. If the time allotted to step 1116 has not yet expired, the device may repeat step 1116 upon polling. If it is determined that the device is not assembled properly on the user's body, the device is deactivated in step 1118. If the device remains in testing steps 1108, 1112, and/or 1116 for a cumulative time period that exceeds the cumulative testing time limit, the device is deactivated in step 1118. Similarly, if the device remains in testing step 1116 for a time period that exceeds a predetermined Stage 4 testing time limit, then the device is deactivated in step 1118. An exemplary Stage 4 testing time limit may range from about five seconds to about one minute, but is not limited to this exemplary range. On the other hand, if it is determined that the device is assembled properly on the user's body, the method proceeds to step 1122 in which the microcontroller determines if the device is in an appropriate state for dosing.

The microcontroller of the device may enter an activation sequence in step 1122 that includes additional testing stages, for example, to determine whether the power supply of the device can deliver sufficient electrical energy. Exemplary activation sequences that may be performed in step 1122 are taught in U.S. patent application Ser. No. 12/648,726, titled "Electronic Control of Drug Delivery System," filed Dec. 29, 2009, the entire contents of which are expressly incorporated herein by reference. If it is determined that the device is not in an appropriate state for dosing in step 1122, the device may be deactivated in step 1124. If the device remains in testing step 1122 for a time period that exceeds a time limit allotted for step 1122, the device is deactivated in step 1124. In the alternative, if the device remains in testing steps 1108, 1112, 1116 and/or 1122 for a cumulative time period that exceeds the cumulative testing time limit, the device is deactivated in step 1124. On the other hand, if it is determined that the device is in an appropriate state for dosing in step 1122, the device may be placed in a state ready for dosing. In this dosing-ready state, the microcontroller may initiate dosing of a therapeutic agent without user input in one embodiment and upon receiving user input in another embodiment (for example, in the form of an activation button press). In a dosing-ready state that requires user input to proceed to dosing, there may be a time limit for the user to provide the required input before the device will be automatically deactivated.

One of ordinary skill in the art will recognize that exemplary methods of verifying the presence and alignment of one or more reservoirs relative to one or more corresponding electrodes may include more or fewer steps than those illustrated in FIG. 11, and that the steps illustrated in FIG. 11 may be performed in a different order than shown. One or more of the steps depicted in FIG. 11 may be repeated as described in further detail with reference to FIGS. 12-15.

Figure 12:
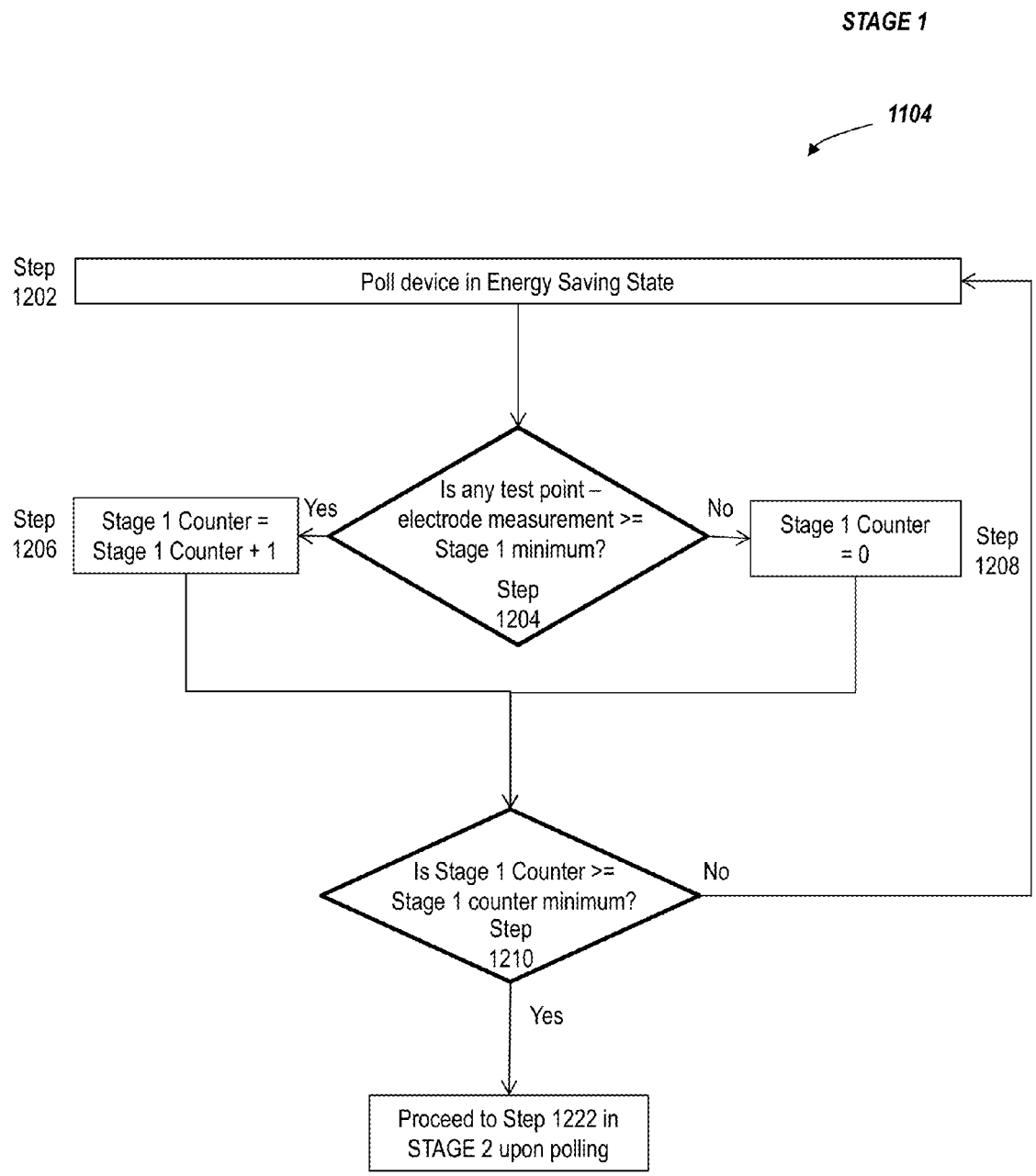
FIGS. 12, 13A, 13B, 14A, 14B, 15A, and 15B are flowcharts corresponding to FIG. 11 illustrating an exemplary method of verifying the presence and alignment of one or more reservoirs relative to one or more corresponding electrodes in an iontophoretic drug delivery device.

FIG. 12 is a flowchart illustrating an exemplary embodiment of step 1104 (Stage 1) of FIG. 11 in more detail. As described above, Stage 1 determines if the device is being assembled. In step 1202, the device is polled at a predetermined time interval while in the energy saving state. If the device is being assembled (that is, if at least one reservoir is positioned over the electrodes and their associated test points), an electrical connection is established between at least one electrode and at least one of its associated test points. That is, detection of a minimum electrical connectivity between at least one electrode and at least one of its associated test points indicates that the device is being assembled by a user. Upon polling, in step 1204, the microcontroller determines if the electrical connectivity between at least one electrode and at least one of its associated test points is greater than (or equal to or greater than) a predetermined Stage 1 minimum value, which indicates that the reservoir is being assembled with the electrode. If this is the case, then a Stage 1 Counter is incremented by one in step 1206; otherwise, the Stage 1 counter is set to zero in step 1208. An exemplary Stage 1 minimum value for the electrical connectivity may be represented as a maximum resistance of about 50,000 to about 60,000 ohms, although other values may be used. In an exemplary embodiment, the Stage 1 minimum value is represented by a maximum resistance of about 56,400 ohms. One of ordinary skill in the art will recognize that other exemplary minimum and maximum values may be used based on, for example, resistance of the animal body. Exemplary electrical paths that may be used in performing step 1204 are described with reference to FIGS. 8A-8E.

Upon setting the Stage 1 counter in step 1206 or 1208, the microcontroller determines, in step 1210, if the Stage 1 counter is greater than (or equal to or greater than) a predetermined Stage 1 counter minimum. If this is the case, the method proceeds to step 1222 of Stage 2 illustrated in FIGS. 12A and 12B upon polling; otherwise, the method returns to step 1202. An exemplary Stage 1 counter minimum may range from 2 to 15, but is not limited to this exemplary range. Waiting until the Stage 1 Counter becomes equal to or greater than a minimum ensures that a minimum electrical connectivity is detected for a minimum continuous period of time. This eliminates the possibility that the electrical connectivity detected is due to sudden transient changes in the system or environment, for example, lightning bolts, and provides confidence that the detected electrical connectivity is the result of assembly of the device.

Figure 13A:
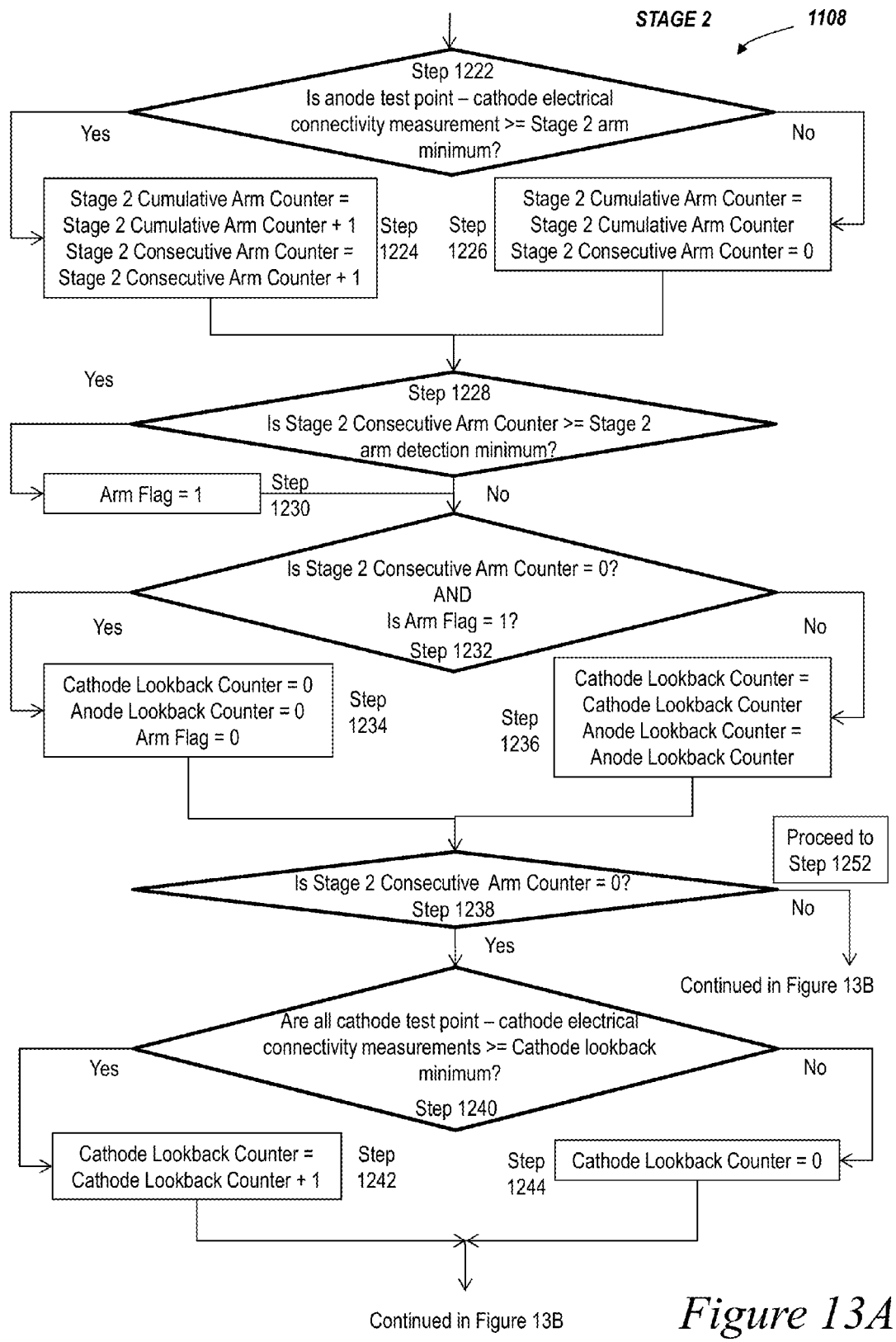
Figure 13B:
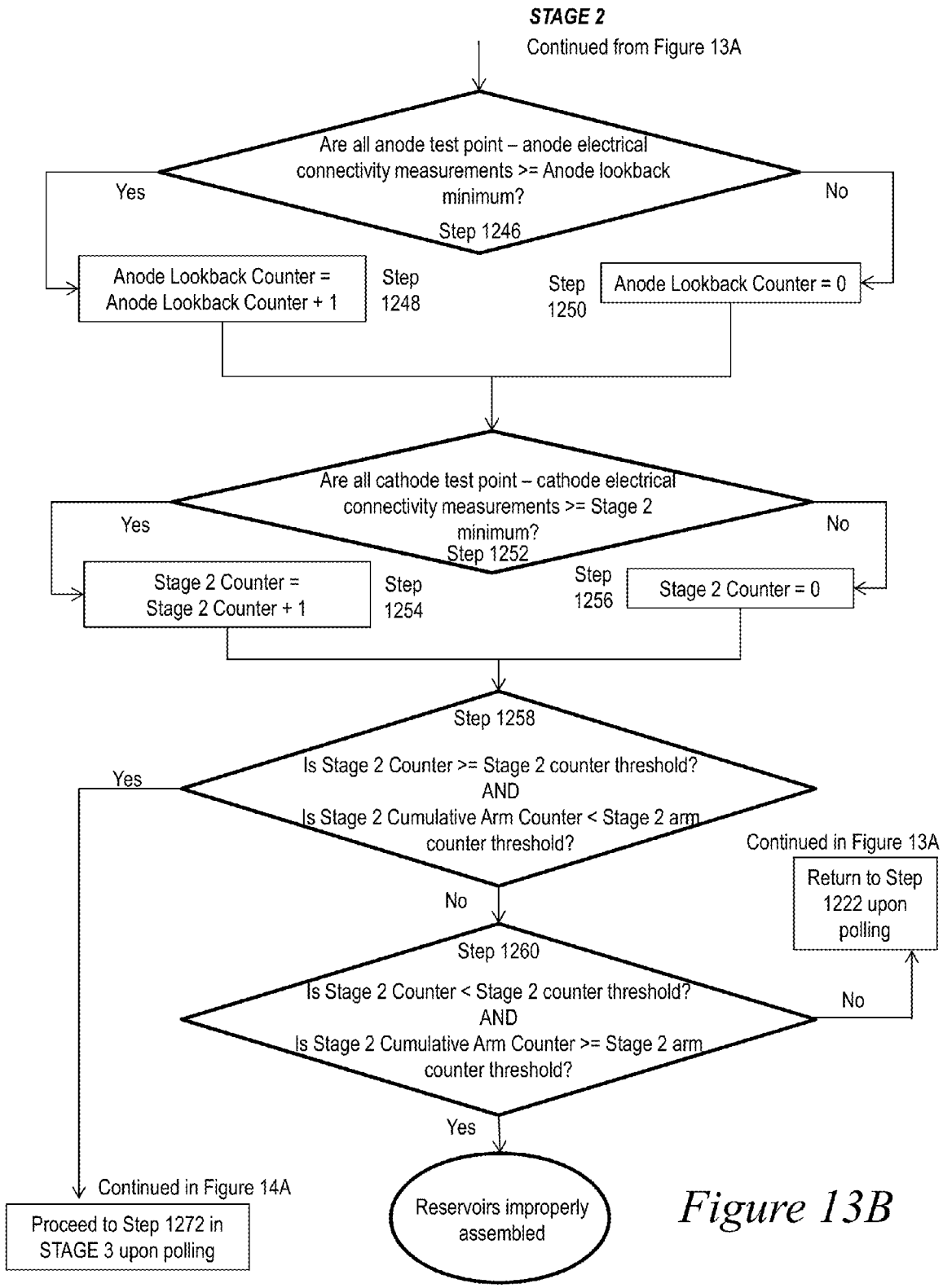

FIGS. 13A and 13B are flowcharts illustrating an exemplary embodiment of step 1108 (Stage 2) of FIG. 11 in more detail. As described above, Stage 2 determines if the device is being assembled properly. In step 1222, upon polling of the device, the microcontroller determines if the electrical connectivity across the electrodes is greater than (or equal to or greater than) a predetermined Stage 2 arm minimum, which indicates that the device is placed on the user's body such that an electrical connection is established between the electrodes. If this is the case, then a Stage 2 Cumulative Arm Counter is incremented by one and a Stage 2 Consecutive Arm Counter is incremented by one in step 1224. Otherwise, the Stage 2 Cumulative Arm Counter is maintained at its current value and the Stage 2 Consecutive Arm Counter is set to zero in step 1226. An exemplary Stage 2 arm counter minimum value may be represented as a maximum resistance of about 10,000 to about 20,000 ohms, but is not limited to this exemplary range. In an exemplary embodiment, the Stage 2 arm counter minimum value may be represented as a maximum resistance of about 16,000 ohms. One of ordinary skill in the art will recognize that other exemplary minimum and maximum values may be used based on, for example, resistance of the animal body. Exemplary electrical paths that may be used in performing step 1222 are described with reference to FIG. 16.

Upon setting the counters in step 1224 or 1226, the microcontroller determines, in step 1228, if the Stage 2 Consecutive Arm Counter is greater than (or equal to or greater than) a Stage 2 arm detection minimum value, which indicates that the device has been placed on the user's body during assembly for a minimum continuous period of time. If this is the case, then an Arm Flag is set to one in step 1230 to indicate this fact, whereupon the method proceeds to step 1232. On the other hand, if the Stage 2 Consecutive Arm Counter is not greater than the Stage 2 arm detection minimum value, then the method proceeds directly to step 1232 from step 1228. An exemplary Stage 2 Consecutive Arm Counter may range from about 2 to 15, but is not limited to this exemplary range.

Figure 14A:
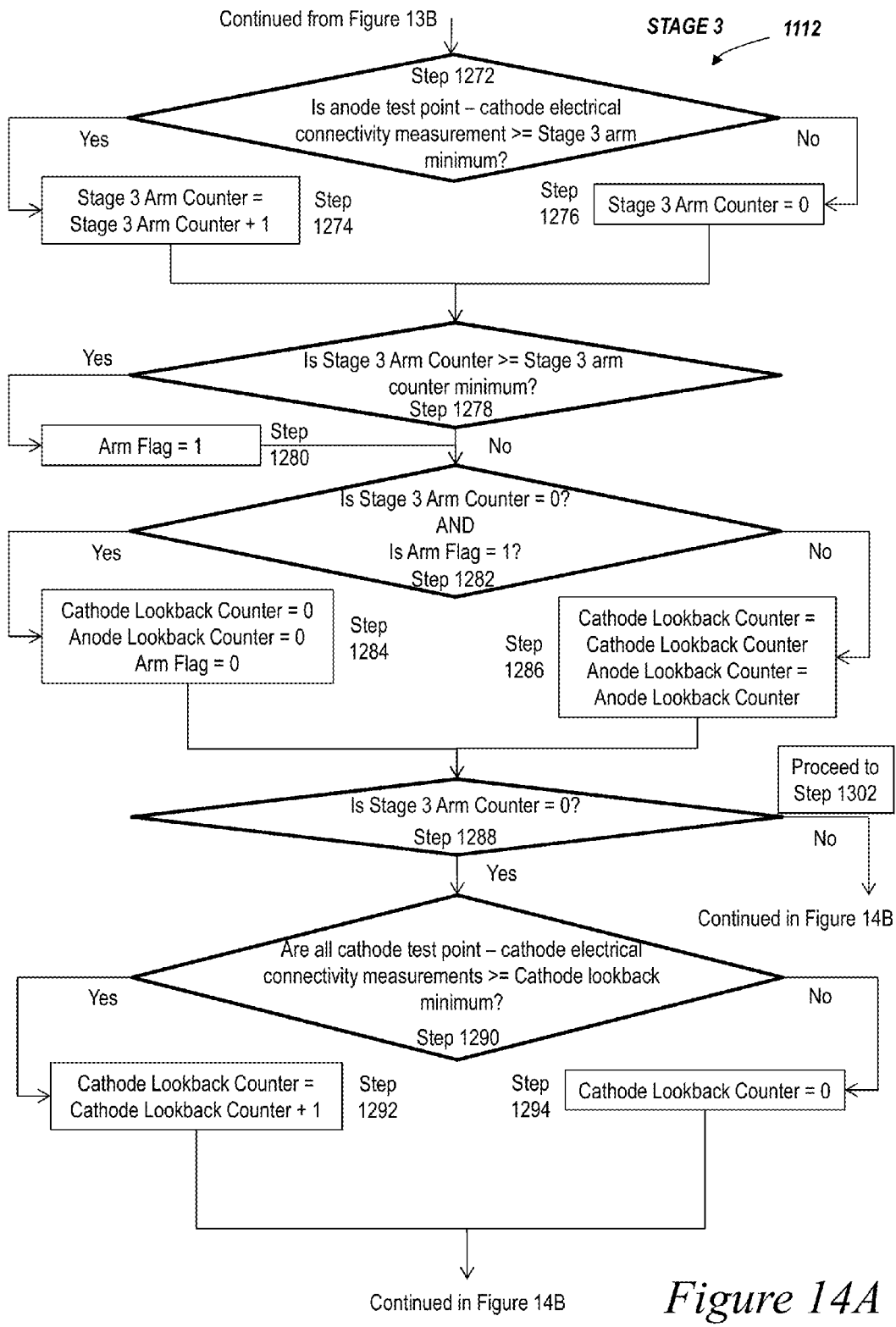
Figure 14B:
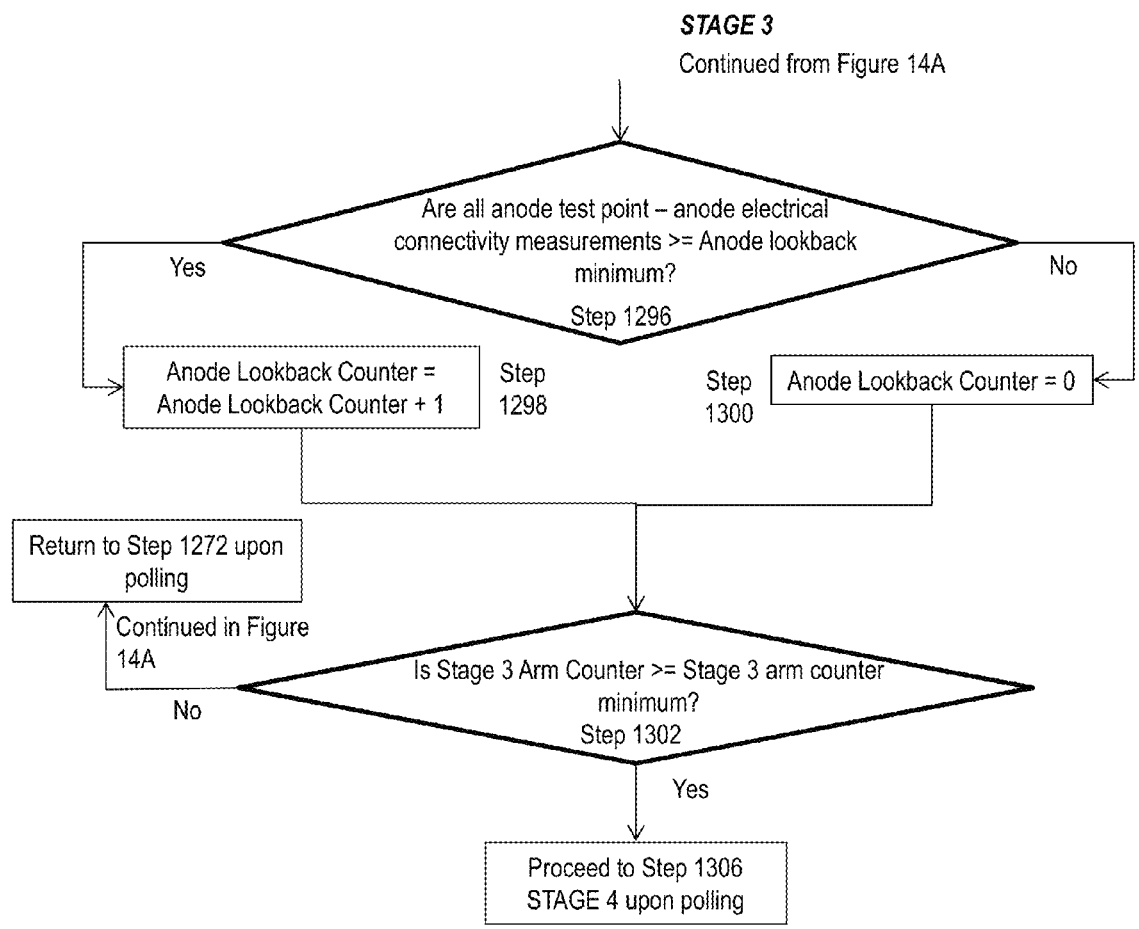

In step 1232, the microcontroller determines if the Stage 2 Consecutive Arm Counter is equal to zero and if the Arm Flag is equal to one. If both of these conditions are satisfied in step 1232, then the Arm Flag is set to zero to indicate that the device is no longer on the user's body and a Cathode Lookback Counter and an Anode Lookback Counter are each set to zero in step 1234. On the other hand, if both of the conditions are not satisfied in step 1232, then the Cathode Lookback Counter and the Anode Lookback Counter are each maintained at their current values in step 1236. Values of the Cathode Lookback Counter and the Anode Lookback Counter may be used in Stage 4 as illustrated in FIGS. 14A and 14B.

Upon setting the counters in step 1234 or 1236, the microcontroller determines, in step 1238, if the Stage 2 Consecutive Arm Counter is equal to zero, which indicates that the device is not currently on the user's body. If this is the case, then the method proceeds to step 1240. If the Stage 2 Consecutive Arm Counter is not equal to zero, then the method proceeds directly from step 1238 to step 1252.

In step 1240, the microcontroller determines if the electrical connectivity between the cathode and its associated test points is greater than (or equal to or greater than) a cathode lookback minimum value, which indicates that a reservoir is properly assembled with the cathode. If this is the case, then the Cathode Lookback Counter is incremented by one in step 1242; otherwise, the Cathode Lookback Counter is set to zero in step 1244. An exemplary cathode lookback minimum value may be represented as a maximum resistance of about 1,000 to about 2,000 ohms, but is not limited to this exemplary range. In an exemplary embodiment, the cathode lookback minimum value may be represented as a maximum resistance of about 1,700 ohms. One of ordinary skill in the art will recognize that other exemplary minimum and maximum values may be used based on, for example, resistance of the animal body. Exemplary electrical paths that may be used in performing step 1240 are described with reference to FIGS. 8A-8E.

Upon setting the counter in step 1242 or 1244, the microcontroller determines, in step 1246, if the electrical connectivity between the anode and its associated test points is greater than (or equal to or greater than) an anode lookback minimum value, which indicates that a reservoir is properly assembled with the anode. If this is the case, then the Anode Lookback Counter is incremented by one in step 1248; otherwise, the Anode Lookback Counter is set to zero in step 1250. Upon setting the counter in step 1248 or 1250, the method proceeds to step 1252. An exemplary anode lookback minimum value used in step 1246 may be represented as a maximum resistance of about 10,000 to about 20,000 ohms, but is not limited to this exemplary range. In an exemplary embodiment, the anode lookback minimum value may be represented as a maximum resistance of about 15,800 ohms. One of ordinary skill in the art will recognize that other exemplary minimum and maximum values may be used based on, for example, resistance of the animal body. Exemplary electrical paths that may be used in performing step 1246 are described with reference to FIGS. 8A-8E.

In step 1252, the microcontroller determines if the electrical connectivity between the cathode and its associated test points is greater than (or equal to or greater than) a Stage 2 minimum value, indicating that a reservoir is properly assembled with the cathode based on the Stage 2 cathode minimum value used. If this is the case, a Stage 2 Counter is incremented by one in step 1254; otherwise, the Stage 2 Counter is set to zero in step 1256. An exemplary Stage 2 cathode minimum value used in step 1252 may be represented as a maximum resistance of about 100,000 to about 200,000 ohms, but is not limited to this exemplary range. In an exemplary embodiment, the Stage 2 cathode minimum value may be represented as a maximum resistance of about 135,000 ohms. One of ordinary skill in the art will recognize that other exemplary minimum and maximum values may be used based on, for example, resistance of the animal body. One of ordinary skill in the art will recognize that electrical connectivity between the anode and its associated test points may be used alternatively in step 1252. Exemplary electrical paths that may be used in performing step 1252 are described with reference to FIGS. 8A-8E.

Upon setting the counter in step 1254 or 1256, the microcontroller determines, in step 1258, if the Stage 2 Counter is greater than (or equal to or greater than) a Stage 2 counter threshold and if the Stage 2 Cumulative Arm Counter is lower than (or equal to or lower than) a Stage 2 arm counter threshold. If both of these conditions are satisfied in step 1258, this indicates that the device is assembled properly and that the device was not on the user's body for too long during assembly, and the method proceeds to step 1272 of Stage 3 illustrated in FIGS. 14A and 14B. On the other hand, if either or both conditions are not satisfied in step 1258, the method proceeds to step 1260. In step 1260, the microcontroller determines if the Stage 2 Counter is lower than (or equal to or lower than) the Stage 2 counter threshold and if the Stage 2 Cumulative Arm Counter is greater than (or equal to or greater than) the Stage 2 arm counter threshold, which indicates that the device is not assembled properly and was placed on the user's body for too long during assembly. If both of the conditions are satisfied in step 1260, this indicates that the reservoirs may have been placed off-center on the user's body, which can cause burning of the user's body. As such, the microcontroller determines that the device is improperly assembled and the device is deactivated. Otherwise, if either or both conditions are not satisfied in step 1260, then the method returns to step 1222 upon polling. An exemplary Stage 2 counter threshold may range from 2 to 15, but is not limited to this exemplary range. An exemplary Stage 2 arm counter threshold may range from 2 to 15, but is not limited to this exemplary range.

FIGS. 14A and 14B are flowcharts illustrating an exemplary embodiment of step 1112 (Stage 3) of FIG. 11 in more detail. As described above, Stage 3 determines if the device is placed on the user's body. In step 1272, upon polling of the device, the microcontroller determines if the electrical connectivity across the electrodes is greater than (or equal to or greater than) a Stage 3 arm minimum value, which indicates that the device is placed on the user's body such that an electrical connection is established between the electrodes. If this is the case, then a Stage 3 Arm Counter is incremented in step 1274; otherwise, the Stage 3 Arm Counter is set to zero in step 1276. After the counter is set in step 1274 or 1276, the method proceeds to step 1278. An exemplary Stage 3 arm minimum value may be represented as a maximum resistance of about 10,000 to about 20,000 ohms, but is not limited to this exemplary range. An exemplary Stage 3 arm minimum value may be represented as a maximum resistance of about 16,500 ohms. One of ordinary skill in the art will recognize that other exemplary minimum and maximum values may be used based on, for example, resistance of the animal body. Exemplary electrical paths that may be used in performing step 1272 are described with reference to FIG. 16.

In step 1278, the microcontroller determines if the Stage 3 Arm Counter is greater than (or equal to or greater than) a Stage 3 arm counter minimum value, which indicates that the device has been placed on the user's body for a minimum continuous period of time. If this is the case, an Arm Flag is set to one in step 1280, whereupon the method proceeds to step 1282. Otherwise, the method proceeds directly to step 1282 from step 1278. An exemplary Stage 3 arm counter minimum value may range from 2 to 15, but is not limited to this exemplary range.

In step 1282, the microcontroller determines if the Stage 3 Arm Counter is equal to zero and if the Arm Flag is set to one. If both of these conditions are satisfied in step 1282, then the Arm Flag is set to zero to indicate that the device is no longer on the user's body and a Cathode Lookback Counter and an Anode Lookback Counter are each set to zero in step 1284. On the other hand, if both of the conditions are not satisfied in step 1282, then the Cathode Lookback Counter and the Anode Lookback Counter are each maintained at their current values in step 1286. Values of the Cathode Lookback Counter and the Anode Lookback Counter may be used in Stage 4 as illustrated in FIGS. 14A and 14B.

Upon setting the counters in step 1284 or 1286, the microcontroller determines, in step 1288, if the Stage 3 Arm Counter is equal to zero, which indicates that the device is not currently on the user's body. If this is the case, then the method proceeds to step 1290. If the Stage 3 Arm Counter is not equal to zero, then the method proceeds directly from step 1288 to step 1302.

In step 1290, the microcontroller determines if the electrical connectivity between the cathode and its associated test points is greater than (or equal to or greater than) a cathode lookback minimum value, which indicates that a reservoir is properly assembled with the cathode. If this is the case, then the Cathode Lookback Counter is incremented by one in step 1292; otherwise, the Cathode Lookback Counter is set to zero in step 1294. An exemplary cathode lookback minimum value may be represented as a maximum resistance of about 1,000 to about 2,000 ohms, but is not limited to this exemplary range. In an exemplary embodiment, the cathode lookback minimum value is about 1,700 ohms. One of ordinary skill in the art will recognize that other exemplary minimum and maximum values may be used based on, for example, resistance of the animal body. Exemplary electrical paths that may be used in performing step 1290 are described with reference to FIGS. 8A-8E.

Upon setting the counter in step 1292 or 1294, the microcontroller determines, in step 1296, if the electrical connectivity between the anode and its associated test points is greater than (or equal to or greater than) an anode lookback minimum value, which indicates that a reservoir is properly assembled with the anode. If this is the case, then the Anode Lookback Counter is incremented by one in step 1298; otherwise, the Anode Lookback Counter is set to zero in step 1300. Upon setting the counter in step 1298 or 1300, the method proceeds to step 1302. An exemplary anode lookback minimum value may be represented as a maximum resistance of about 10,000 to about 20,000 ohms, but is not limited to this exemplary range. In an exemplary embodiment, the anode lookback minimum value is about 15,800 ohms. One of ordinary skill in the art will recognize that other exemplary minimum and maximum values may be used based on, for example, resistance of the animal body. Exemplary electrical paths that may be used in performing step 1296 are described with reference to FIGS. 8A-8E.

In step 1302, the microcontroller determines if the Stage 3 Arm Counter is greater than (or equal to or greater than) a Stage 3 arm counter minimum, which indicates that the device has been placed on the user's body for a minimum continuous period of time. If this is the case, the method proceeds to step 1306 of Stage 4 illustrated in FIGS. 15A and 15B; otherwise, the method returns to step 1272 upon polling. An exemplary Stage 3 arm counter minimum may range from 2 to 15, but is not limited to this exemplary range.

Figure 15A:
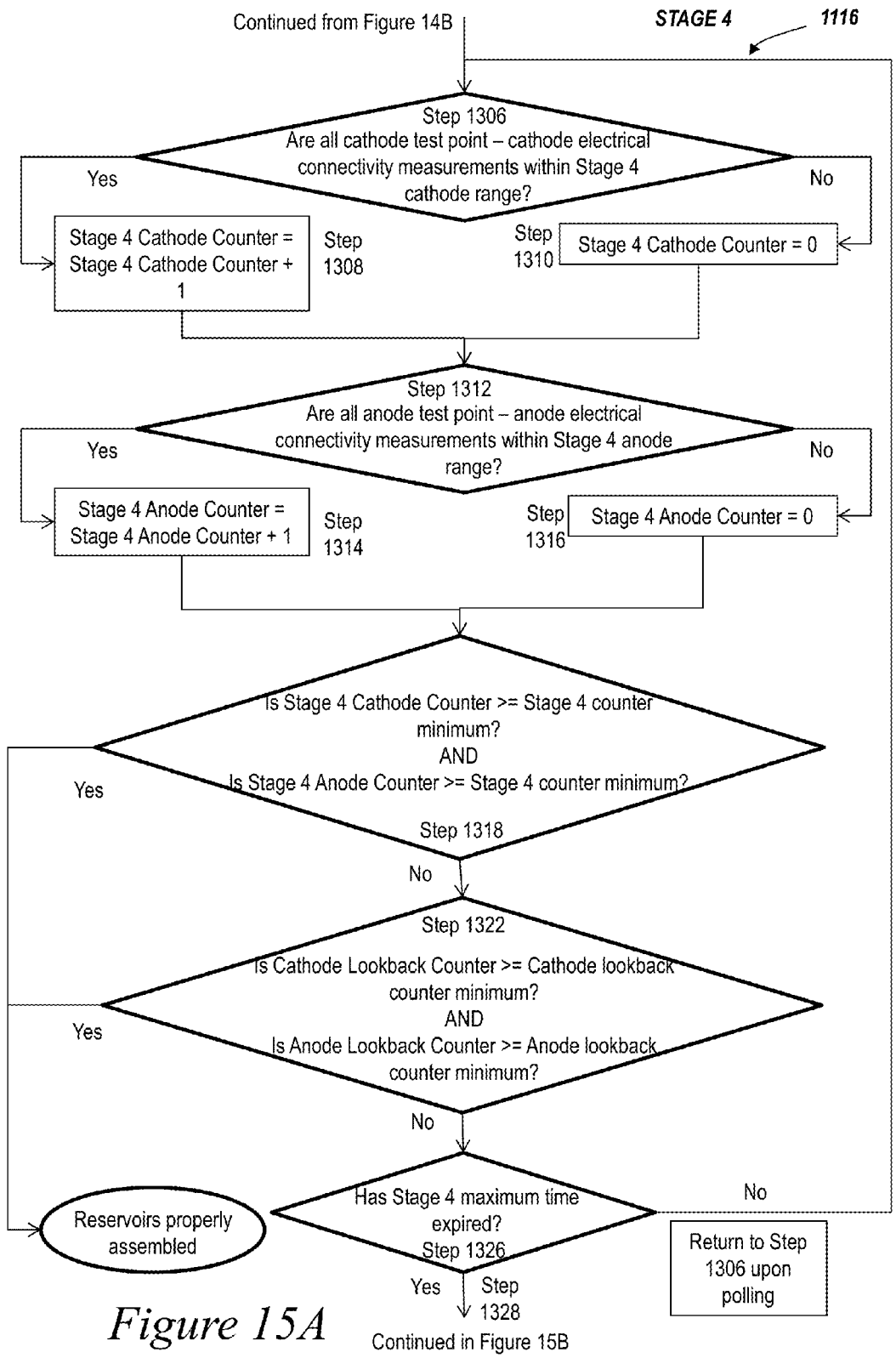
Figure 15B:
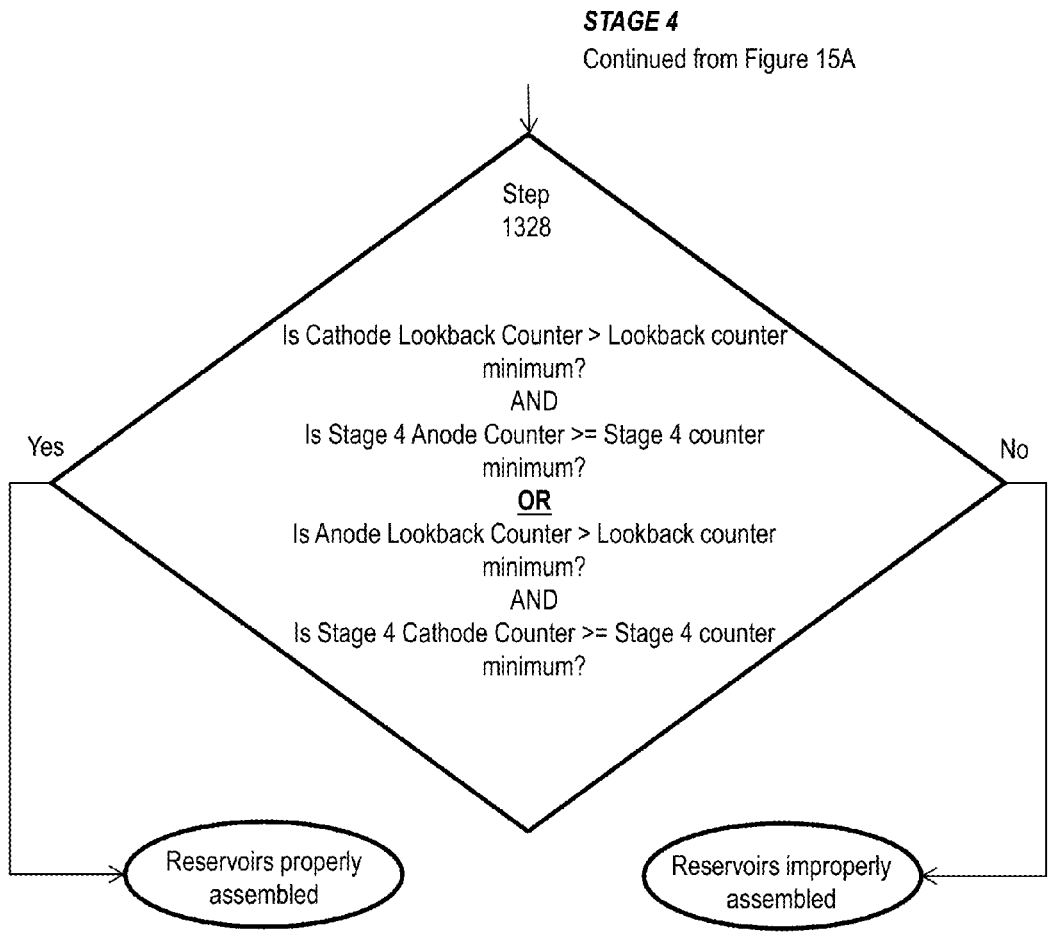

FIGS. 15A and 15B are flowcharts illustrating an exemplary embodiment of step 1116 (Stage 4) of FIG. 11 in more detail. As described above, Stage 4 determines if the device has been properly assembled on the user's body. In step 1306, upon polling of the device, the microcontroller determines if the electrical connectivity between the cathode and each of its associated test points falls within a Stage 4 acceptable cathode range, which indicates that a reservoir is properly assembled with the cathode. If this is the case, then a Stage 4 Cathode Counter is incremented by one in step 1308; otherwise, the Stage 4 Cathode Counter is set to zero in step 1310. An exemplary Stage 4 acceptable cathode range may be represented as a maximum resistance of about 800 to about 1000 ohms and a minimum resistance of about 400 to about 600 ohms, but is not limited to this exemplary range. An exemplary Stage 4 acceptable cathode range may be represented as a maximum resistance of about 1100 ohms and a minimum resistance of about 100 ohms. One of ordinary skill in the art will recognize that other exemplary minimum and maximum values may be used based on, for example, resistance of the animal body. Exemplary electrical paths that may be used in performing step 1306 are described with reference to FIGS. 8A-8E.

After the counter is set in step 1308 or 1310, the method proceeds to step 1312. In step 1312, the microcontroller determines if the electrical connectivity between the anode and each of its associated test points falls within a Stage 4 acceptable anode range, which indicates that a reservoir is properly assembled with the anode. If this is the case, then a Stage 4 Anode Counter is incremented by one in step 1314; otherwise, the Stage 4 Anode Counter is set to zero in step 1316. After the counter is set in step 1314 or 1316, the method proceeds to step 1318. An exemplary Stage 4 acceptable anode range may be represented as a maximum resistance of about 700 to about 900 ohms and a minimum resistance of about 50 to about 150 ohms, but is not limited to this exemplary range. An exemplary Stage 4 acceptable anode range may be represented as a maximum resistance of about 1000 ohms and a minimum resistance of about 100 ohms. One of ordinary skill in the art will recognize that other exemplary minimum and maximum values may be used based on, for example, resistance of the animal body. Exemplary electrical paths that may be used in performing step 1312 are described with reference to FIGS. 8A-8E.

In step 1318, the microcontroller determines if the Stage 4 Cathode Counter is greater than (or equal to or greater than) a Stage 4 cathode counter minimum value and if the Stage 4 Anode Counter is greater than (or equal to or greater than) a Stage 4 anode counter minimum value, indicating that the reservoirs are properly assembled with the electrodes. If both conditions are satisfied in step 1318, then the microcontroller determines that the device is properly assembled. Otherwise, if one or both conditions are not satisfied in step 1318, then the method proceeds from step 1318 to step 1322. An exemplary Stage 4 cathode counter minimum value may range from 2 to 15, but is not limited to this exemplary range. An exemplary Stage 4 anode counter minimum value may range from 2 to 15, but is not limited to this exemplary range.

The conditions in step 1318 may not be satisfied if one or more test points fail when the device is placed on the user's body. To account for these cases, the microcontroller looks back to the electrical connectivity determined in Stage 3 to determine if the stored electrical connectivity satisfies thresholds to indicate that the device was properly assembled in Stage 3. In step 1322, the microcontroller determines if the electrode lookback counters indicate that the electrodes were properly assembled in prior stages of testing. More particularly, in step 1322, the microcontroller determines if the Cathode Lookback Counter is greater than (or equal to or greater than) a cathode lookback counter minimum value, and if the Anode Lookback Counter is greater than (or equal to or greater than) an anode lookback counter minimum value. If both conditions are satisfied in step 1322, then the microcontroller determines that the device is properly assembled. Otherwise, if one or both conditions are not satisfied in step 1322, then the method proceeds to step 1326. An exemplary cathode lookback counter minimum value may range from 2 to 15, but is not limited to this exemplary range. An exemplary anode lookback counter minimum value may range from 2 to 15, but is not limited to this exemplary range.

The microcontroller allows a maximum period of time for successful completion of Stage 4 of testing. The maximum time period may range from about 5 seconds to about 30 seconds, but is not limited to this exemplary range. In step 1326, the microcontroller determines whether this maximum time period has expired. If the maximum time period has not expired, the method returns to step 1306 upon polling. Otherwise, if the maximum time period has expired, the method proceeds to step 1328.

In step 1328, the microcontroller determines if a combination of Stage 4 electrode counters and electrode lookback counters indicate that the electrodes are properly assembled. More particularly, in step 1328, the microcontroller determines if at least one of two conditions are satisfied. The first condition assessed in step 1328 is satisfied if the Cathode Lookback Counter is greater than (or equal to or greater than) a cathode lookback counter minimum value and if the Stage 4 Anode Counter is greater than (or equal to or greater than) the Stage 4 anode counter minimum value. The second condition assessed in step 1328 is satisfied if the Anode Lookback Counter is greater than (or equal to or greater than) an anode lookback counter minimum value and if the Stage 4 Cathode Counter is greater than (or equal to or greater than) the Stage 4 cathode counter minimum value. If one or both conditions are satisfied in step 1328, then the microcontroller determines that the device is properly assembled. Otherwise, if neither condition is satisfied in step 1328, then the microcontroller determines that the device is improperly assembled. The counter minimum values used in step 1328 may range from 2 to 15, but are not limited to this exemplary range.

Figure 17:
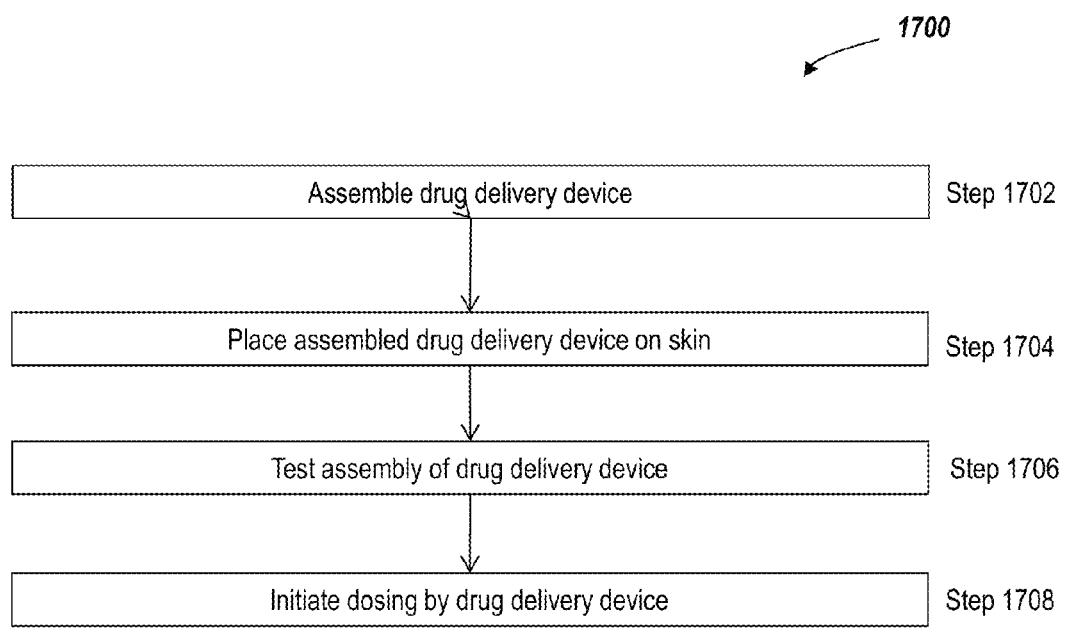
FIG. 17 is a flowchart illustrating an exemplary method of using an exemplary iontophoretic drug delivery device.

FIG. 17 illustrates a flowchart illustrating an exemplary method 1700 of using an exemplary iontophoretic drug delivery device. In step 1702, in an exemplary embodiment, a user assembles the reservoirs and electrodes provided separately in the device packaging so that the reservoirs are placed on and aligned with the electrodes. In step 1704, the user places the assembled device on the user's skin. In step 1706, the user waits while the device is in a testing mode until the device provides an indication that the device is ready for use. In step 1708, once the device is ready for use, the user presses an activation button to initiate administration of a therapeutic agent contained in the device.

Figure 18:
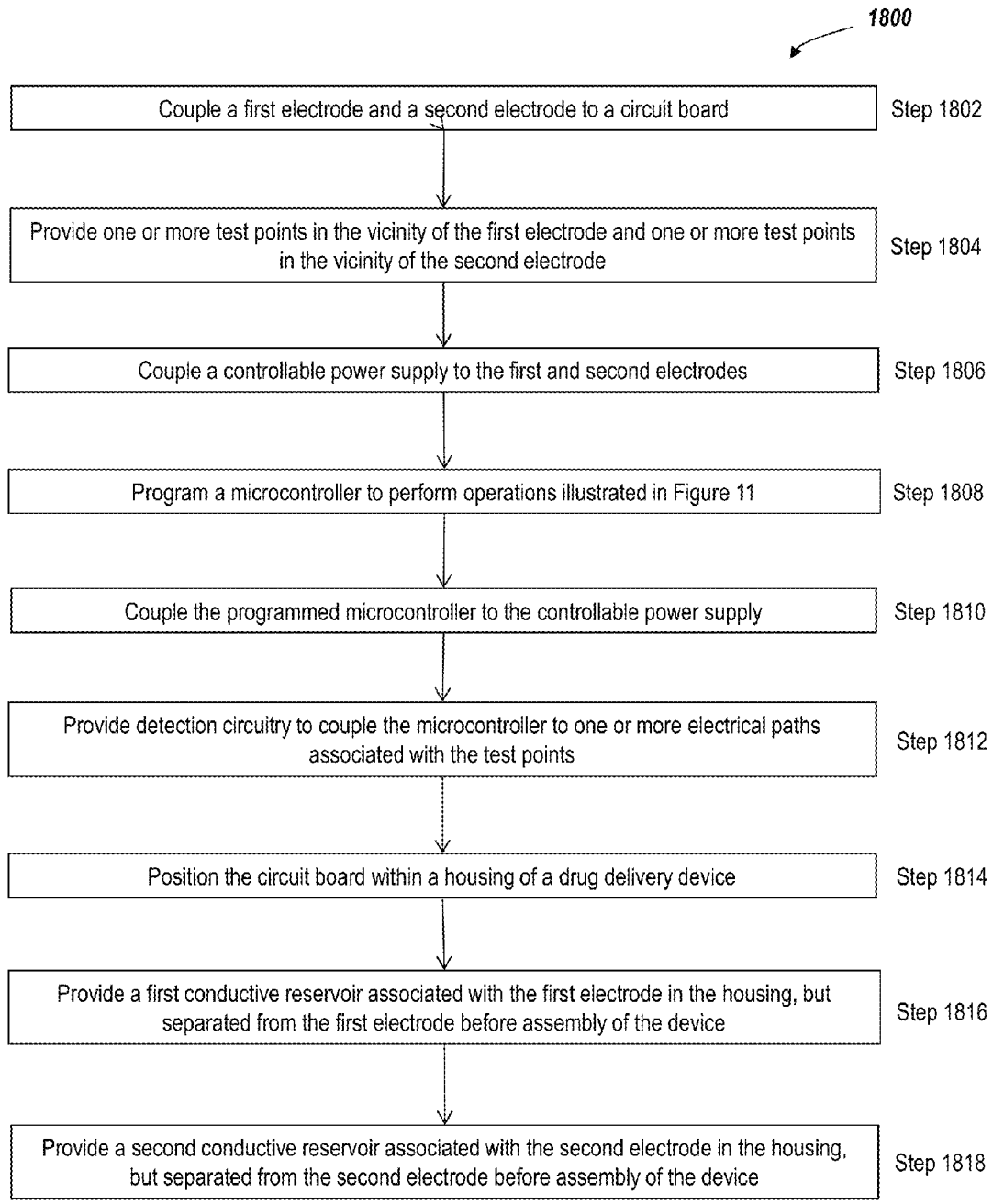
FIG. 18 is a flowchart illustrating an exemplary method of fabricating an exemplary iontophoretic drug delivery device.

FIG. 18 is a flowchart illustrating an exemplary method 1800 for fabricating an exemplary iontophoretic drug delivery device including a system for testing whether the device has been properly assembled. In step 1802, a first electrode (e.g., an anode or a cathode) and a second electrode (e.g., a cathode or an anode) are coupled or affixed to a circuit board. In step 1804, one or more electrical test points are coupled or affixed to the circuit board so that the test points are separated from and in the vicinity of the first electrode. Similarly, one or more electrical test points are affixed to the circuit board so that the test points are separated from and in the vicinity of the second electrode. In step 1806, a controllable power supply is electrically coupled to the first and second electrodes. In step 1808, a microcontroller is programmed to perform exemplary operations taught herein, for example, the operations illustrated in FIG. 11. In step 1810, the microcontroller is electrically coupled to the controllable power supply. In step 1812, detection circuitry is provided on the circuit board to electrically couple the microcontroller to one or more electrical paths associated with the test points. In step 1814, the assembled circuit board is positioned within an outer housing of the drug delivery device. In step 1816, a first conductive reservoir associated with the first electrode is provided in the housing or external to the housing, so that the first reservoir is separated from the first electrode before assembly by a user. In step 1818, a second conductive reservoir associated with the second electrode is provided in the housing or external to the housing, so that the second reservoir is separated from the second electrode before assembly by a user.

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

What is claimed is:

1. A system for testing whether an iontophoretic device is in an appropriate state for administering a therapeutic agent into an animal body by driving an electrotransport current through a surface of the animal body, the system for testing comprising:
   at least one electrical test point;
   at least one electrical path leading from the at least one test point and configured to lead to an electrode of the iontophoretic device; and
   a controller programmed to:
      measure an electrical characteristic of the at least one electrical path,
      determine whether the iontophoretic device is in the appropriate state for administering a therapeutic agent into the animal body from the measured electrical characteristic, wherein the measured electrical characteristic indicates that the iontophoretic device is in the appropriate state for administering the therapeutic agent into the animal body when the therapeutic agent is properly disposed with respect to the iontophoretic device, and
      prevent use of the iontophoretic device if the iontophoretic device is not in the appropriate state for administering the therapeutic agent into the animal body within a fixed predetermined period of time after a first measurement of the electrical characteristic.

2. The system for testing of claim 1, wherein the therapeutic agent is introduced into a reservoir before the reservoir is assembled with the electrode.

3. The system for testing of claim 1, wherein the therapeutic agent is introduced into a reservoir after the reservoir is assembled with the electrode.

4. The system for testing of claim 1, wherein the iontophoretic device is in the appropriate state for administering the therapeutic agent into the animal body when a reservoir comprising the therapeutic agent is present on a first surface of the electrode, and wherein the controller is programmed to determine whether the reservoir comprising the therapeutic agent is present on the first surface of the electrode based on the measured electrical characteristic.

5. The system for testing of claim 1, wherein the iontophoretic device is in the appropriate state for administering the therapeutic agent into the animal body when a reservoir comprising the therapeutic agent covers a first surface of the electrode such that no portion of the first surface of the electrode is exposed to the surface of the animal body, and wherein the controller is programmed to determine whether the reservoir comprising the therapeutic agent covers the entire first surface of the electrode based on the measured electrical characteristic.

6. The system for testing of claim 1, wherein the iontophoretic device is in the appropriate state for administering the therapeutic agent into the animal body when a reservoir comprising the therapeutic agent covers a first surface of a cathode electrode, and wherein the controller is programmed to verify that the reservoir covering the first surface of the cathode electrode comprises the therapeutic agent as opposed to a nontherapeutic agent associated with an anode electrode of the iontophoretic device based on the measured electrical characteristic.

7. The system for testing of claim 1, wherein the at least one electrical path is selected from a group comprising a path leading from a first test point and configured to lead to the electrode, and a path leading from a plurality of tied test points and configured to lead to the electrode.

8. The system for testing of claim 7, wherein the measured electrical characteristic is a conductivity of the at least one electrical path, and wherein the controller is programmed to determine whether the iontophoretic device is in the appropriate state for administering the therapeutic agent into the animal body based on the fact that conductivity greater than a predefined conductivity threshold indicates that the iontophoretic device is in the appropriate state.

9. The system for testing of claim 1, further comprising:
   a power supply for applying a voltage across the at least one electrical path for measuring the electrical characteristic.

10. The system for testing of claim 1, wherein the controller is programmed to deactivate the iontophoretic device upon a determination that a reservoir is not properly attached to a first surface of the electrode.

11. The system for testing of claim 1, wherein the at least one test point comprises a plurality of discrete test points disposed around the electrode.

12. The system for testing of claim 1, wherein the at least one test point comprises at least one electrical test point that contiguously surrounds at least a portion of the electrode.

13. The system for testing of claim 1, further comprising:
   a second electrical path leading across a cathode electrode and an anode electrode of the iontophoretic device;
   wherein the controller is further programmed to:
      measure a second electrical characteristic of the second electrical path, and
      determine whether the iontophoretic device is in the appropriate state for administering the therapeutic agent into the animal body from the measured second electrical characteristic;
   wherein the iontophoretic device is in the appropriate state for administering the therapeutic agent into the animal body when the therapeutic agent is positioned and aligned over either the anode electrode or the cathode electrode.

14. The system for testing of claim 1, wherein the controller is further programmed to determine whether the iontophoretic device is in the appropriate state for administering the therapeutic agent into the animal body from the measured electrical characteristic before the electrode is placed in direct or indirect contact with the surface of the animal body;

wherein the measured electrical characteristic indicates improper attachment of a reservoir to a first surface of the electrode.

15. The system for testing of claim 1, wherein the controller is further programmed to determine whether the iontophoretic device is in the appropriate state for administering the therapeutic agent into the animal body from the measured electrical characteristic after the electrode is placed in direct or indirect contact with the surface of the animal body;

wherein the measured electrical characteristic indicates improper attachment of a reservoir to a first surface of the electrode.

16. A system for testing whether an iontophoretic device is in an appropriate state for administering a therapeutic agent into an animal body by driving an electrotransport current through a surface of the animal body, the system for testing comprising:

a first electrical test point and a second electrical test point;

at least one electrical path leading from the first test point and configured to lead to the second test point; and a controller programmed to:
measure an electrical characteristic of the at least one electrical path,
determine whether the iontophoretic device is in the appropriate state for administering a therapeutic agent into the animal body from the measured electrical characteristic, wherein the measured electrical characteristic indicates that the iontophoretic device is in the appropriate state for administering the therapeutic agent into the animal body when the therapeutic agent is properly disposed with respect to the iontophoretic device, and
prevent use of the iontophoretic device if the iontophoretic device is not in the appropriate state for administering the therapeutic agent into the animal body within a fixed predetermined period of time after a first measurement of the electrical characteristic.

17. The system for testing of claim 16, wherein the iontophoretic device is in the appropriate state for administering the therapeutic agent into the animal body when a reservoir comprising the therapeutic agent is present on a first surface of the electrode, and wherein the controller is programmed to determine whether the reservoir comprising the therapeutic agent is present on the first surface of the electrode based on the measured electrical characteristic.

18. The system for testing of claim 16, wherein the iontophoretic device is in the appropriate state for administering the therapeutic agent into the animal body when a reservoir comprising the therapeutic agent covers a first surface of the electrode such that no portion of the first surface of the electrode is exposed to the surface of the animal body, and wherein the controller is programmed to determine whether the reservoir comprising the therapeutic agent covers the first surface of the electrode based on the measured electrical characteristic.

19. The system for testing of claim 16, wherein the iontophoretic device is in the appropriate state for administering the therapeutic agent into the animal body when a reservoir comprising the therapeutic agent covers a first surface of an anode electrode, and wherein the controller is programmed to verify that the reservoir covering the first surface of the anode electrode comprises the therapeutic agent, as opposed to a nontherapeutic agent associated with a cathode electrode of the iontophoretic device, based on the measured electrical characteristic.

20. The system for testing of claim 16, wherein the controller is programmed to deactivate the iontophoretic device upon a determination that a reservoir is not properly attached to a first surface of the electrode.

21. A method for testing whether an iontophoretic device is in an appropriate state for administering a therapeutic agent into an animal body by driving an electrotransport current through a surface of the animal body, the method comprising:

applying a voltage across at least one electrical path leading from at least one electrical test point and configured to lead to an electrode of the iontophoretic device;

measuring an electrical characteristic of the at least one electrical path using a controller;

determining whether the iontophoretic device is in an appropriate state for administering a therapeutic agent from the measured electrical characteristic, wherein the measured electrical characteristic indicates that the iontophoretic device is in the appropriate state for administering the therapeutic agent into the animal body when the therapeutic agent is properly disposed with respect to the iontophoretic device; and preventing use of the iontophoretic device if the iontophoretic device is not in the appropriate state for administering the therapeutic agent into the animal body within a fixed predetermined period of time after a first measurement of the electrical characteristic.

22. The method for testing of claim 21, wherein the iontophoretic device is in the appropriate state for administering the therapeutic agent into the animal body when a reservoir comprising the therapeutic agent is present on a first surface of the electrode, and wherein the method comprises:

determining, based on the measured electrical characteristic, whether the reservoir comprising the therapeutic agent is present on the first surface of the electrode.

23. The method for testing of claim 21, wherein the iontophoretic device is in the appropriate state for administering the therapeutic agent into the animal body when a reservoir comprising the therapeutic agent covers a first surface of the electrode such that no portion of the first surface of the electrode is exposed to the surface of the animal body, and wherein the method comprises:

determining, based on the measured electrical characteristic, whether the reservoir comprising the therapeutic agent covers the entire first surface of the electrode.

24. The method for testing of claim 21, wherein the iontophoretic device is in the appropriate state for administering the therapeutic agent into the animal body when a reservoir comprising the therapeutic agent covers a first surface of a cathode electrode, and wherein the method comprises:

verifying, based on the measured electrical characteristic, that the reservoir covering the first surface of the cathode electrode comprises the therapeutic agent as opposed to a nontherapeutic agent associated with an anode electrode of the iontophoretic device.

25. The method for testing of claim 21, further comprising:

deactivating the iontophoretic device upon a determination that a reservoir is not properly attached to a first surface of the electrode.

26. A method for testing whether an iontophoretic device is in an appropriate state for administering a therapeutic agent into an animal body by driving an electrotransport current through a surface of the animal body, the method comprising:
  applying a voltage across at least one electrical path leading from at least one test point associated with an anode and configured to lead to at least one test point associated with a cathode;
  measuring an electrical characteristic of the at least one electrical path;
  determining whether the iontophoretic device is in an appropriate state for administering a therapeutic agent from the measured electrical characteristic, wherein the measured electrical characteristic indicates that the iontophoretic device is in the appropriate state for administering the therapeutic agent into the animal body when the therapeutic agent is properly disposed with respect to the iontophoretic device; and
  preventing use of the iontophoretic device if the iontophoretic device is not in the appropriate state for administering the therapeutic agent into the animal body within a fixed predetermined period of time after a first measurement of the electrical characteristic.

27. A method for fabricating a testing assembly for an iontophoretic device that administers a therapeutic agent into an animal body by driving an electrotransport current through a surface of the animal body, the method comprising:
  providing at least one test point in proximity to an electrode of the iontophoretic device;
  providing at least one electrical path leading from the at least one test point and configured to lead to the electrode;
  coupling an electrical power supply to the at least one electrical path to enable a voltage to be applied across the at least one electrical path; and
  programming a controller to:
    measure an electrical characteristic of the at least one electrical path,
    determine whether the iontophoretic device is in an appropriate state for administering a therapeutic agent from the measured electrical characteristic, wherein the measured electrical characteristic indicates that the iontophoretic device is in the appropriate state for administering the therapeutic agent into the animal body when the therapeutic agent is properly disposed with respect to the iontophoretic device, and
    prevent use of the iontophoretic device if the iontophoretic device is not in the appropriate state for administering the therapeutic agent into the animal body within a fixed predetermined period of time after a first measurement of the electrical characteristic.

* * * * *